US008229559B2

(12) United States Patent
Westendorp et al.

(10) Patent No.: US 8,229,559 B2
(45) Date of Patent: Jul. 24, 2012

(54) EVALUATION OF IMPLANTABLE MEDICAL DEVICE DATA

(75) Inventors: Hendrikus A. Westendorp, Edina, MN (US); Cygni Chan, St. Paul, MN (US); Amisha S. Patel, Maple Grove, MN (US); Denise Dirnberger, Blaine, MN (US); Jean K. Ringold, Ramsey, MN (US); Kevin T. Ousdigian, Shoreview, MN (US); Robert B. Trojan, Brooklyn Park, MN (US); Nelson H. Soken, Hugo, MN (US); Karen J. Kleckner, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 140 days.

(21) Appl. No.: 12/837,320

(22) Filed: Jul. 15, 2010

(65) Prior Publication Data

US 2012/0016432 A1 Jan. 19, 2012

(51) Int. Cl.
*A61N 1/00* (2006.01)
(52) U.S. Cl. .......................................... 607/9
(58) Field of Classification Search .................. 607/9, 4, 607/5, 17; 600/510, 515, 518, 529; 705/2
See application file for complete search history.

(56) References Cited

U.S. PATENT DOCUMENTS

| | | | |
|---|---|---|---|
| 5,193,550 A | 3/1993 | Duffin | |
| 5,379,776 A | 1/1995 | Murphy et al. | |
| 5,509,927 A | 4/1996 | Epstein et al. | |
| 5,527,344 A | 6/1996 | Arzbaecher et al. | |
| 5,722,999 A | 3/1998 | Snell | |
| 5,755,739 A | 5/1998 | Sun et al. | |
| 5,776,168 A | 7/1998 | Gunderson | |
| 6,270,457 B1 | 8/2001 | Bardy | |
| 6,358,203 B2 | 3/2002 | Bardy | |
| 6,393,316 B1 | 5/2002 | Gillberg et al. | |
| 6,470,210 B1 | 10/2002 | Chen et al. | |
| 6,599,250 B2 | 7/2003 | Webb et al. | |
| 6,607,485 B2 | 8/2003 | Bardy | |
| 6,669,631 B2 | 12/2003 | Norris et al. | |
| 6,748,269 B2 | 6/2004 | Thompson et al. | |
| 6,974,413 B2 | 12/2005 | Bardy | |
| 6,980,860 B2 | 12/2005 | Stadler et al. | |
| 7,047,083 B2 | 5/2006 | Gunderson et al. | |
| 7,069,085 B2 | 6/2006 | Cao et al. | |
| 7,206,633 B2 | 4/2007 | Saba | |
| 7,212,849 B2 | 5/2007 | Zhang et al. | |
| 7,236,828 B2 | 6/2007 | Casavant et al. | |
| 7,286,997 B2 | 10/2007 | Spector et al. | |
| 7,289,851 B2 | 10/2007 | Gunderson et al. | |
| 7,333,855 B2 | 2/2008 | Gunderson et al. | |
| 7,353,063 B2 | 4/2008 | Simms, Jr. | |

(Continued)

*Primary Examiner* — George Manuel
*Assistant Examiner* — Robert N Wieland

(57) ABSTRACT

A system includes an episode classification module and a data retrieval module. The episode classification module receives electrograms (EGMs) from N implantable medical devices (IMDs) and determines whether the EGMs are associated with deliveries of therapy by the N IMDs. The episode classification module analyzes at least some of the EGMs and determines whether the deliveries or non-deliveries of therapy by the IMDs were appropriate. The data retrieval module receives a request from a computing device, via a network, that indicates at least two groups of the N IMDs. The data retrieval module provides to the computing device via the network, in response to the request, data for presentation to a user that indicates for each of the groups, at least one of how many of the one or more deliveries or non-deliveries were appropriate, or how many of the one or more deliveries or non-deliveries were inappropriate.

32 Claims, 16 Drawing Sheets

U.S. PATENT DOCUMENTS

| | | |
|---|---|---|
| 7,369,893 B2 | 5/2008 | Gunderson |
| 7,430,446 B2 | 9/2008 | Li |
| 7,480,529 B2 | 1/2009 | Li |
| 7,539,540 B2 | 5/2009 | Gunderson et al. |
| 7,567,835 B2 | 7/2009 | Gunderson et al. |
| 7,582,061 B2 | 9/2009 | Li et al. |
| 7,738,950 B2 | 6/2010 | Johnson et al. |
| 2001/0007053 A1 | 7/2001 | Bardy |
| 2003/0050563 A1 | 3/2003 | Suribhotla et al. |
| 2003/0204215 A1 | 10/2003 | Gunderson et al. |
| 2004/0015197 A1 | 1/2004 | Gunderson |
| 2004/0064161 A1 | 4/2004 | Gunderson et al. |
| 2004/0093240 A1 | 5/2004 | Shah |
| 2005/0022181 A1 | 1/2005 | Fox et al. |
| 2005/0049910 A1 | 3/2005 | Lancaster et al. |
| 2005/0060193 A1 | 3/2005 | Lancaster et al. |
| 2005/0075902 A1 | 4/2005 | Wager et al. |
| 2005/0080347 A1 | 4/2005 | Sheth et al. |
| 2005/0137636 A1 | 6/2005 | Gunderson et al. |
| 2005/0192506 A1 | 9/2005 | Kim et al. |
| 2005/0192836 A1 | 9/2005 | Rossinni et al. |
| 2005/0192844 A1 | 9/2005 | Esler et al. |
| 2006/0064020 A1 | 3/2006 | Burnes et al. |
| 2006/0074331 A1 | 4/2006 | Kim et al. |
| 2006/0074464 A1 | 4/2006 | Subera et al. |
| 2006/0116732 A1 | 6/2006 | Gunderson et al. |
| 2006/0116733 A1 | 6/2006 | Gunderson |
| 2006/0217621 A1 | 9/2006 | Kim et al. |
| 2006/0217769 A1 | 9/2006 | Saba |
| 2006/0235476 A1 | 10/2006 | Gunderson et al. |
| 2006/0281998 A1 | 12/2006 | Li |
| 2007/0061393 A1 | 3/2007 | Moore |
| 2007/0123789 A1 | 5/2007 | Gunderson et al. |
| 2007/0167986 A1 | 7/2007 | Gunderson et al. |
| 2010/0280841 A1* | 11/2010 | Dong et al. ............... 705/2 |

* cited by examiner

| Device | Clinician<br>Entrust, Concerto, Virtuoso,<br>Consulta, Max II | National<br>Entrust, Concerto, Virtuoso,<br>Consulta, Max II |
|---|---|---|
| Episodes in the year<br>Chamber<br>Patients with ICDs<br>Average Follow-up Months | 2009<br>DR, CRTD<br>100<br>12 | 2009<br>DR, CRTD<br>25,000<br>12 |
| | VT/VF | VT/VF |
| # of VT/VF episodes | 120 (Shocked)<br>30 (ATP) | 12,900 (Shocked)<br>4,000 (ATP) |
| | PATIENT DATA | PATIENT DATA |
| % Patients Shocked | 17% | 18% |
| | SHOCKED EPISODE DATA | SHOCKED EPISODE DATA |
| | VT/VF 60%<br>SVT/Noise/Oversensing 40%<br>n = 120 | VT/VF 43%<br>SVT/Noise/Oversensing 57%<br>n = 12900 |

FIG. 11

|          | App. | Inapp. | Indet. |
|----------|------|--------|--------|
| Patient A | 1 | 0 | 0 |
| Patient B | 1 | 1 | 0 |
| Patient C | 1 | 1 | 1 |
| Patient D | 0 | 1 | 0 |
| Patient E | 3 | 0 | 0 |
| Total | 6 | 3 | 1 |
| Percent | 60% | 30% | 10% |

Total Episodes = 10

FIG. 15A

|          | App. | Inapp. | Indet. |
|----------|------|--------|--------|
| Patient A | 1 | 0 | 0 |
| Patient B | 1 | 1 | 0 |
| Patient C | 1 | 1 | 1 |
| Patient D | 0 | 1 | 0 |
| Patient E | 10 | 0 | 0 |
| Total | 13 | 2 | 1 |
| Percent | 81.25% | 12.5% | 6.25% |

Total Episodes = 16

Normalize ↑

Normalized Data

|          | App. | Inapp. | Indet. |
|----------|------|--------|--------|
| Patient A | 1 | 0 | 0 |
| Patient B | 1/2 | 1/2 | 0 |
| Patient C | 1/3 | 1/3 | 1/3 |
| Patient D | 0 | 1 | 0 |
| Patient E | 1 | 0 | 0 |
| Total | 17/6 | 11/6 | 2/6 |
| Percent | 56.6% | 36.6% | 6.6% |

Total Normalized Episodes = 5

FIG. 15B

EVALUATION OF IMPLANTABLE MEDICAL DEVICE DATA

TECHNICAL FIELD

The disclosure relates to systems and methods for evaluating data retrieved from a plurality of implantable medical devices, and, more particularly, to systems and methods for comparing data between subsets of implantable medical devices.

BACKGROUND

An implantable medical device (IMD), such as a cardiac pacemaker or a cardioverter-defibrillator, provides therapeutic electrical stimulation to a patient via electrodes carried by one or more implantable leads. The IMD may provide the electrical stimulation based on sensed physiological parameters of the patient, such as sensed electrical signals via electrodes carried by the implantable leads.

The IMD may detect various types of arrhythmias based on the electrical signals sensed by the IMD. For example, the IMD may detect ventricular tachycardia (VT) or ventricular fibrillation (VF) based on sensed electrical signals. The IMD may provide various electrical therapies in response to detection of VT/VF. Specifically, the IMD may provide one or more defibrillation shocks in response to detection of VT/VF. Additionally, the IMD may provide antitachycardia pacing (ATP) in response to detection of VT in order to remedy the VT before it progresses to VF.

However, identification of VT/VF by the IMD may be subject to error. For example, the IMD may inappropriately characterize a supraventricular tachycardia (SVT) as VT/VF. Also, the IMD may mistakenly detect VT/VF due to oversensing or undersensing. Misidentification of VT/VF due to SVTs, oversensing, or undersensing may result in inappropriate application of electrical therapy by the IMD. Specifically, the IMD may unnecessarily provide a defibrillation shock based on a misidentification of VT/VF due to SVTs, oversensing, or undersensing.

IMDs may store electrogram waveforms (EGMs) that represent the electrical activity of the heart that resulted in identification of the tachyarrhythmia by the IMD and delivery of electrical therapy (e.g., defibrillation shocks). Clinicians may download and review the stored EGMs, marker channel data, and other data to determine whether the electrical therapy was appropriately/inappropriately applied. The clinicians may make the determination based on a characterization of the stored EGM and a type of electrical therapy applied. For example, a clinician may determine that a defibrillation shock was inappropriately applied if the clinician characterizes the EGM associated with the defibrillation shock as representing an SVT or including oversensing or undersensing, since these conditions may not necessitate a defibrillation shock. A clinician may determine that a defibrillation shock was appropriately applied if the clinician characterizes the EGM associated with the defibrillation shock as VT/VF, since these conditions may require a defibrillation shock.

SUMMARY

Typically, the clinician may determine whether IMDs have appropriately or inappropriately diagnosed patient conditions and/or applied therapies on a per patient basis. The clinician typically does not have access to information regarding how other IMDs have performed outside of their clinic. Clinicians may therefore not have information available to compare IMD performance of their clinic to a baseline of IMD performance defined by other clinics. For example, clinicians may not have access to information detailing how many inappropriate/appropriate defibrillation shocks are observed at other clinics, and therefore may not have a baseline for comparison of the number of inappropriate/appropriate shocks at their own clinic.

Access to data from a larger number of IMDs outside of a clinician's practice may provide a baseline for IMD performance for which the clinician may gauge the performance of their own practice. Accordingly, it may be beneficial to the clinician to have access to a system that provides a larger volume of data relating to IMD performance outside of their clinic, e.g., appropriate/inappropriate defibrillation shocks, so that the clinician may have a metric with which to gauge their practice relating to IMD implant, programming, and follow-up.

In general, the disclosure is directed to a system for providing analysis, retrieval, and display of data from a large number of IMDs, e.g., on a national level. The system includes a remote device that receives data, e.g., EGMs, from the IMDs via a network. The remote device performs analysis on the data. For example, for data associated with particular events in which an IMD made a diagnosis and/or delivered a therapy, the remote device may analyze the data to determine whether the diagnosis or therapy was inappropriate or appropriate, e.g., correct or incorrect. The remote device may store the received data, data indicating the IMD diagnosis or therapy, and the result of the remote device analysis in a datastore.

The remote device may present results of its analysis of data retrieved from IMDs to a user, such as a clinician, in response to a request. For example, the remote device may present results of its analysis of data from IMDs associated with a particular clinician or clinic in conjunction with results of its analysis of data from a broader subset of IMDs or from all IMDs. In this manner, the user may evaluate the performance of certain IMDs or clinics relative to larger population of IMDs or clinics.

For example, the remote device may identify EGMs and other data associated with delivery of defibrillation shocks by IMDs, and analyze the EGMs and other data to characterize the EGMs and other data as indicating one of VF, VT, SVT, oversensing, or undersensing. In this manner, the remote device may determine whether the underlying diagnosis and delivery of the defibrillation shocks were appropriate or inappropriate. The remote device may store the analysis and characterization of the EGMs and other data in a datastore.

Clinicians may then use a computing device to send a request to the remote device to retrieve the analysis data and characterization of the EGMs and other data. The remote device may retrieve data from the datastore in response to the request and send the data to the clinician's computing device which displays the data as a dashboard on the computing device. Using the system, a clinician may have access to a volume of information received from a large number of IMDs. Based on the information, the clinician may determine a baseline performance of IMDs and then use the baseline as a metric to gauge performance of IMDs with which they are associated, e.g., via implantation or follow-up.

Knowledge of the baseline data and subsequent comparison may allow the clinician to determine if, and where, there may be room for improvement in their practice. For example, the clinician may determine whether programming changes for IMDs or selection of different types of IMDs for future implant is advisable based on comparison of their data to the baseline data. The clinician may generate subsequent dashboards in the future determine whether their practice has improved relative to the baseline due to any changes made as a result of information retrieved from prior dashboards.

In one example, the present disclosure is directed to a system comprising an episode classification module and a data retrieval module. The episode classification module receives electrogram waveforms (EGMs) from N implantable medical devices (IMDs) and determines whether the EGMs are associated with one or more deliveries of therapy by the N IMDs. N is an integer greater than 1. The episode classification module analyzes at least some of the EGMs and determines whether the one or more deliveries or non-deliveries of therapy by the IMDs in response to rhythms included in the EGMs were appropriate based on the analysis. The data retrieval module receives a request from a computing device, via a network, the request indicating at least two groups of the N IMDs. The data retrieval module provides to the computing device via the network, in response to the request, data for presentation to a user of the computing device, the data indicating, for each of the groups, at least one of how many of the one or more deliveries or non-deliveries of therapy were appropriate, or how many of the one or more deliveries or non-deliveries of therapy were inappropriate.

In another example, the present disclosure is directed to a method comprising receiving electrogram waveforms (EGMs) from N implantable medical devices (IMDs) and determining whether the EGMs are associated with one or more deliveries of therapy by the N IMDs. N is an integer greater than 1. The method further comprises analyzing at least some of the EGMs and determining whether the one or more deliveries or non-deliveries of therapy by the IMDs in response to rhythms included in the EGMs were appropriate based on the analysis. The method further comprises receiving a request from a computing device, via a network, the request indicating at least two groups of the N IMDs. Additionally, the method comprises providing to the computing device via the network, in response to the request, data for presentation to a user of the computing device, the data indicating, for each of the groups, at least one of how many of the one or more deliveries or non-deliveries of therapy were appropriate, or how many of the one or more deliveries or non-deliveries of therapy were inappropriate.

The details of one or more examples are set forth in the accompanying drawings and the description below. Other features, objects, and advantages will be apparent from the description and drawings, and from the claims.

BRIEF DESCRIPTION OF THE DRAWINGS

FIG. 11 illustrates an example representation of data collected by the remote device of FIG. 8.

FIG. 15A illustrates an example calculation that may be used to determine relative percentages of appropriate, inappropriate, and indeterminate shocked episodes.

FIG. 15B illustrates another example calculation that may be used to determine relative percentages of appropriate, inappropriate, and indeterminate shocked episodes.

DETAILED DESCRIPTION

Figure 1:
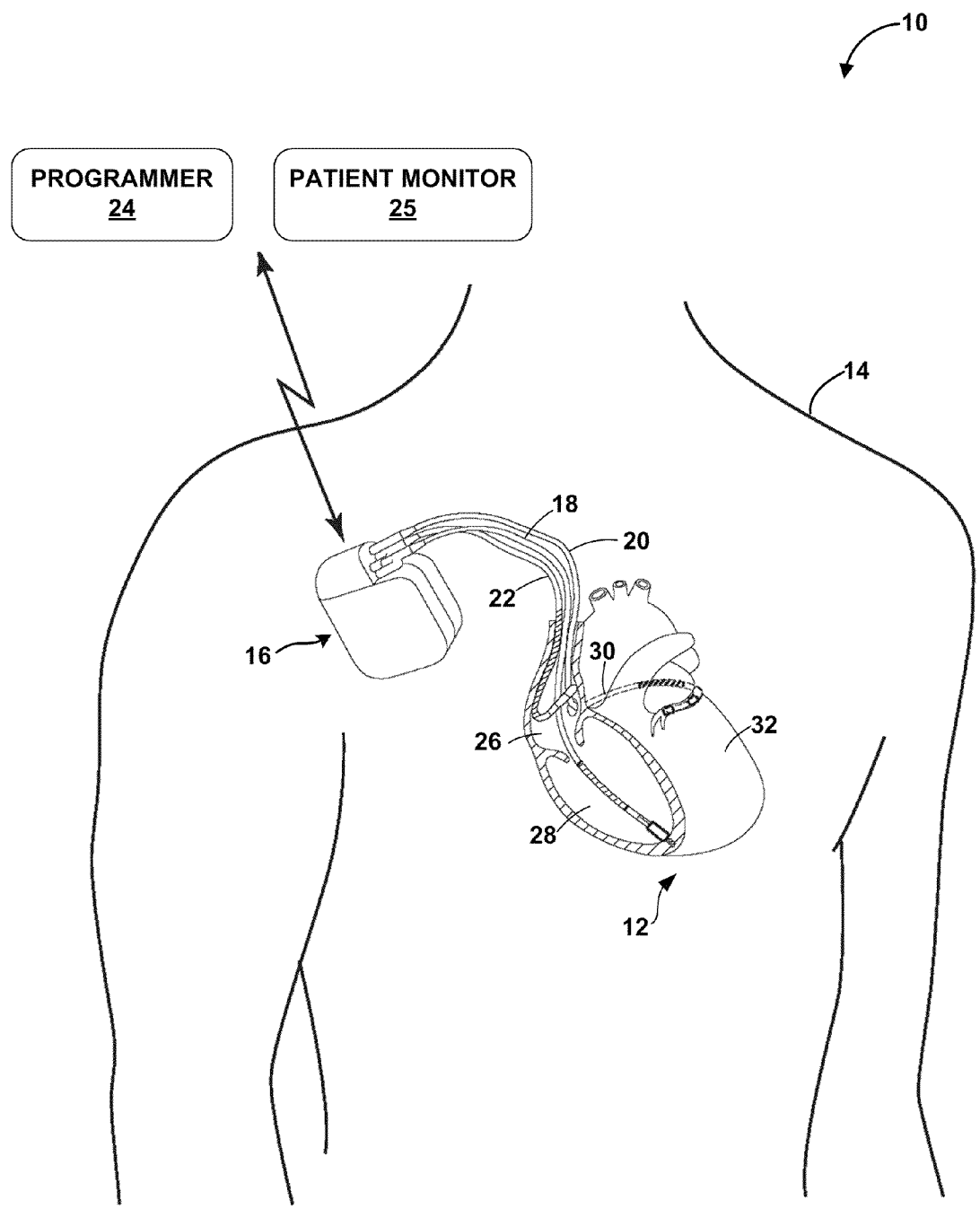
FIG. 1 is a conceptual diagram of an example diagnostic system comprising an implantable medical device (IMD) for delivering stimulation therapy to a heart of a patient via implantable leads.

FIG. 1 is a conceptual diagram of an example system 10 that may be used to diagnose conditions of and provide therapy to a heart 12 of a patient 14. System 10 includes an IMD 16, which is coupled to leads 18, 20, and 22. For example, IMD 16 may be an implantable pacemaker, cardioverter, and/or defibrillator that provides electrical signals to heart 12 using one or more of leads 18, 20, 22.

Leads 18, 20, 22 extend into heart 12 of patient 14. Leads 18, 20, 22 sense electrical activity of heart 12 and/or deliver electrical stimulation to heart 12. Right ventricular (RV) lead 18 extends into right ventricle 28 of heart 12 through one or more veins (not shown), the superior vena cava (not shown), and right atrium 26. Left ventricular (LV) coronary sinus lead 20 extends through one or more veins, the vena cava, right atrium 26, and into coronary sinus 30 to a region adjacent to the free wall of left ventricle 32 of heart 12. Right atrial (RA) lead 22 extends into right atrium 26 of heart 12 through one or more veins and the vena cava.

System 10 includes a programmer 24 that communicates with IMD 16. Programmer 24 may be a handheld computing device, desktop computing device, a networked computing device, etc. Accordingly, programmer 24 may be a computing device that includes a computer-readable storage medium having instructions that cause a processor of programmer 24 to provide the functions attributed to programmer 24 in the present disclosure. System 10 may also include a patient monitor 25. Patient monitor 25 may be a device that reads data from IMD 16 and uploads the data to a server, e.g., automatically or in response to a command from a patient or other user.

Although shown together in FIG. 1 for ease of illustration, programmer 24 and patient monitor 25 may, but typically will not, be co-located. Instead, programmer 24 and patient monitor 25 may individually communicate with IMD 16 when co-located with IMD 16 at respective times. For example, programmer 24 may be used by a clinician in a clinical setting to communicate with IMD 16, and patient monitor 25 may communicate with IMD 16 in a patient's home, automatically or in response to a user command.

Programmer 24 may retrieve data stored in IMD 16 and/or program the operation of IMD 16, e.g., to monitor patient 14 and/or to provide various therapies to patient 14. Programmer 24 may also receive data from IMD 16 in real-time. Accordingly, a user may retrieve data from IMD 16 and program IMD 16 using programmer 24. For example, the user may include a physician, a technician, a surgeon, an electrophysiologist, or other clinician. Data retrieved from IMD 16 using programmer 24 includes waveforms that indicate electrical activity of heart 12. The waveforms retrieved from the IMD 16 may be referred to as cardiac electrogram waveforms or, more particularly in cases in which the waveforms are detected via an intracardiac electrode, intracardiac electrogram waveforms. Cardiac electrogram waveforms stored by IMD 16 and retrieved by programmer 24 may be referred to as "EGMs." Data retrieved from IMD 16 using programmer 24 may also include marker channel data. Marker channel data may indicate the occurrence and timing of sensing, diagnosis, and therapy events associated with IMD 16. Other types of data that may be retrieved from IMD 16 using programmer 24 are also described herein.

Although programmer 24 is illustrated as communicating with IMD 16, programmer 24 may communicate with additional or alternative implantable or external devices that provide electrical stimulation to patient 14 and/or measure electrical potentials or other physiological signals associated with patient 14. For example, programmer 24 may communicate with other forms of cardiac monitors, such as insertable cardiac monitors that monitor heart rhythms and record ECGs associated with physiological events, e.g., fainting. As a further example, programmer 24 may communicate with an implantable neurostimulator (not shown) that provides at least one of deep brain stimulation, vagus nerve stimulation, and spinal cord stimulation, for example. In such examples, programmer 24 may receive an electroencephalogram (EEG) or other neurological electrogram from the implantable neurostimulator, as well as from an external device. In other examples, programmer 24 may receive other signals from other implantable and external medical devices. Accordingly, programmer 24 may receive a plurality of different electrogram waveforms depending on the devices connected to programmer 24.

The programmer 24 may retrieve various types of stored or real-time data from IMD 16. For example, programmer 24 may retrieve EGMs from IMD 16, trends in the rhythm of heart 12 over time, or other sensed physiological parameters of the patient 14, such as intracardiac or intravascular pressure, activity, posture, respiration, or thoracic impedance. Additionally, data may include information regarding the performance or integrity of IMD 16 or other components of diagnostic system 10, such as leads 18, 20, 22, or a power source of IMD 16.

A user may program IMD 16 using programmer 24. Programming IMD 16 may include, for example, setting values for operational parameters, programming a therapy progression, selecting electrodes used to deliver defibrillation pulses, selecting waveforms for the defibrillation pulses, or selecting or configuring a fibrillation detection algorithm for the IMD 16. In general, a defibrillation pulse may refer to an electrical pulse (i.e., shock) that is delivered to heart 12 to correct a potentially life threatening cardiac arrhythmia such as ventricular fibrillation (VF) or ventricular tachycardia (VT). The user may also use programmer 24 to program other therapies provided by IMD 16, such as cardioversion or pacing therapies.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near an implant site of IMD 16 in order to improve the quality or security of communication between IMD 16 and programmer 24.

Patient monitor 25 may be a handheld computing device, desktop computing device, a networked computing device, etc. Patient monitor 25 may include similar functionality as programmer 24. Specifically, patient monitor 25 may retrieve various types of stored or real-time data from IMD 16. For example, patient monitor 25 may retrieve EGMs from IMD 16, trends in the rhythm of heart 12 over time, or other sensed physiological parameters of patient 14, such as intracardiac or intravascular pressure, activity, posture, respiration, or thoracic impedance. Patient monitor 25 may also retrieve marker channel data from IMD 16. Additionally, patient monitor 25 may retrieve information regarding the performance or integrity of IMD 16 or other components of diagnostic system 10, such as leads 18, 20, 22, or a power source of IMD 16. Patient monitor 25 may transfer data from IMD 16 to a clinic or to a remote device through a network.

Figure 2:
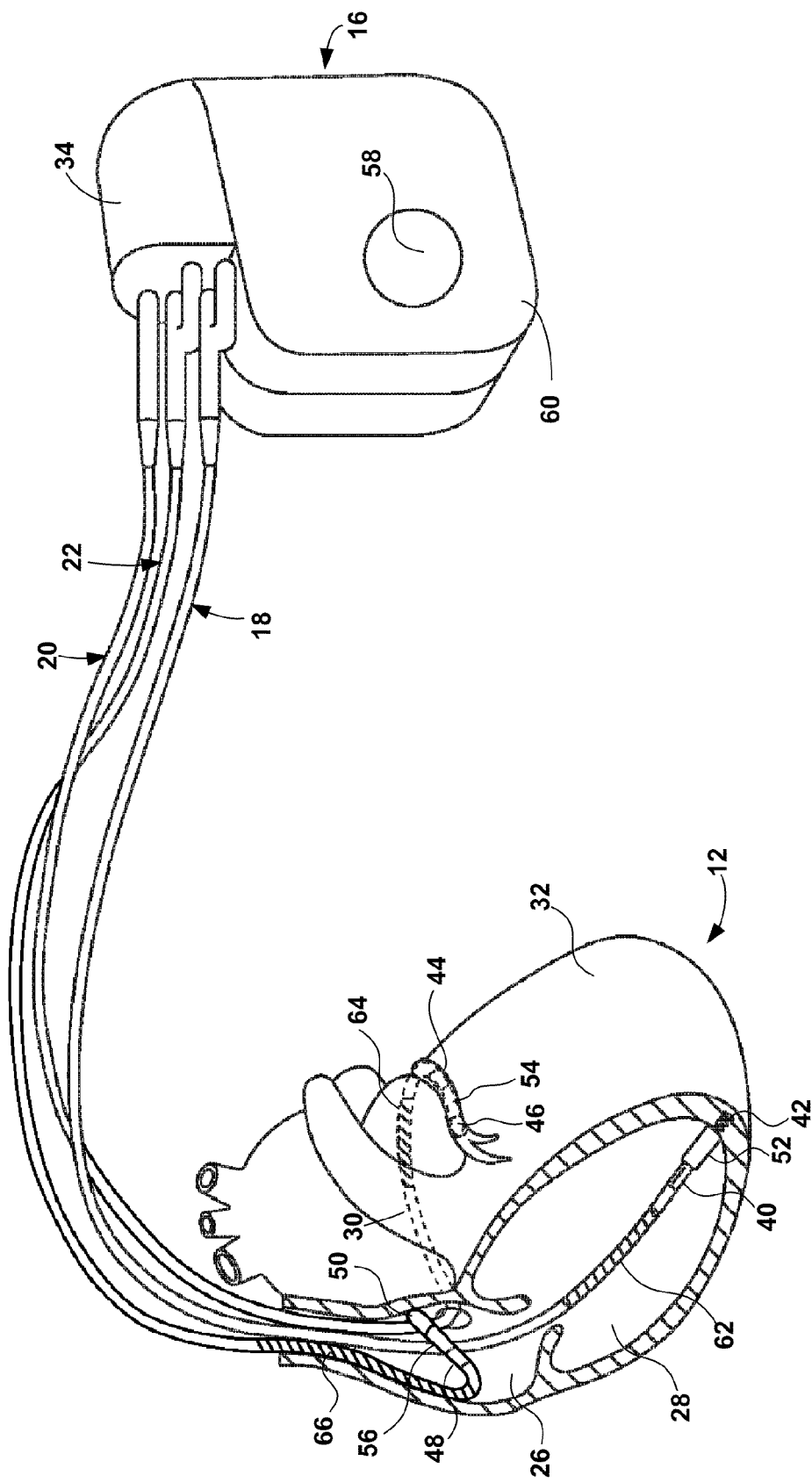
FIG. 2 is a conceptual diagram the IMD and the implantable leads of the system of FIG. 1 in conjunction with the heart.

FIG. 2 is a conceptual diagram illustrating IMD 16 and leads 18, 20, 22 of system 10 in greater detail. IMD 16 includes a housing 60 and a connector block 34. Leads 18, 20, 22 are mechanically and electrically coupled to IMD 16 via connector block 34. Housing 60 may enclose a signal generator that generates therapeutic stimulation, such as cardiac pacing pulses and defibrillation pulses, as well as a sensing module for monitoring the rhythm of heart 12. Leads 18, 20, 22 are coupled to a signal generator and a sensing module of IMD 16 via connector block 34. IMD 16 may sense electrical signals attendant to the depolarization and repolarization of heart 12 via leads 18, 20, 22. IMD 16 may also provide electrical stimulation to heart 12 via leads 18, 20, 22.

IMD 16 may provide pacing pulses to heart 12 based on the electrical signals sensed within heart 12. IMD 16 may also provide defibrillation and/or cardioversion therapy to heart 12. For example, IMD 16 may detect arrhythmia of heart 12, such as fibrillation of the ventricles 28 and 32, and deliver cardioversion or defibrillation therapy to heart 12 in the form of electrical pulses. In some implementations, IMD 16 may be programmed to deliver a progression of therapies, e.g., pulses with increasing energy levels, until a tachyarrhythmia of heart 12 is stopped. IMD 16 may detect tachycardia or fibrillation employing one or more tachycardia or fibrillation detection techniques known in the art.

Leads 18, 20, 22 include electrodes 40, 42, 44, 46, 48, 50, 62, 64, and 66, respectively. IMD 16 may sense electrical signals via electrodes 40, 42, 44, 46, 48, 50, 62, 64, and 66. IMD 16 may also provide electrical stimulation to heart 12 using electrodes 40, 42, 44, 46, 48, 50, 62, 64, and 66. Although each of leads 18, 20, 22 of FIG. 2 includes three electrodes, other configurations of electrodes are contemplated. For example, each of the three leads 18, 20, 22 may include more or less than three electrodes.

Bipolar electrodes 40 and 42 are located adjacent to the distal end of lead 18 in right ventricle 28. Bipolar electrodes 44 and 46 are located adjacent to the distal end of lead 20 in coronary sinus 30. Bipolar electrodes 48 and 50 are located adjacent to the distal end of lead 22 in right atrium 26. There are no electrodes located in the left atrium in the illustrated example, however, other examples may include electrodes in left atrium.

Electrodes 40, 44, and 48 may take the form of ring electrodes. Electrodes 42, 46, and 50 may take the form of extendable helix tip electrodes mounted retractably within insulative electrode heads 52, 54, and 56, respectively. In other embodiments, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil.

IMD 16 includes a housing electrode 58, which may be formed integrally with an outer surface of the hermetically-sealed housing 60 of IMD 16 or otherwise coupled to housing 60. Although a single housing electrode 58 is illustrated in FIG. 2, IMD 16 may include more or less than a single housing electrode 58.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor coupled to housing electrode 58. IMD 16 may sense such electrical signals via any bipolar combination of electrodes 40, 42, 44, 46, 48, 50, 58, 62, 64, and 66. Furthermore, any of electrodes 40, 42, 44, 46, 48, 50, 62, 64, and 66 may be used for unipolar sensing in combination with housing electrode 58.

Any multipolar combination of two or more of electrodes 40, 42, 44, 46, 48, 50, 58, 62, 64, and 66 may be considered a sensing electrode configuration. Usually, but not necessarily, a sensing electrode configuration is a bipolar electrode combination on the same lead, such as electrodes 40 and 42 of lead 18. On a lead having three electrodes, there may be at least three different sensing electrode configurations available to IMD 16. In some implementations, IMD 16 may use sensing electrode configurations having electrodes on two different leads. These sensing electrode configurations with respect to lead 18 are, for the example, tip electrode 42 and ring electrode 40, tip electrode 42 and elongated electrode 62, and ring electrode 40 and elongated electrode 62.

IMD 16 may deliver pacing pulses via a unipolar or bipolar combination of electrodes. IMD 16 delivers pacing pulses via bipolar combinations of electrodes 40, 42, 44, 46, 48 and 50 to produce depolarization of cardiac tissue of heart 12. IMD 16 may deliver pacing pulses via any of electrodes 40, 42, 44, 46, 48 and 50 in combination with housing electrode 58 in a unipolar configuration.

IMD 16 may deliver cardioversion and/or defibrillation shocks to heart 12 via any combination of elongated electrodes 62, 64, 66, and housing electrode 58. Electrodes 58, 62, 64, 66 may also be used to deliver cardioversion pulses to the heart 12.

The electrode configuration of diagnostic system 10 illustrated in FIGS. 1 and 2 is merely one example electrode configuration. In other examples, a diagnostic system may include epicardial leads and/or patch electrodes instead of or in addition to the transvenous leads 18, 20, 22 illustrated in FIG. 1.

Although IMD 16 of FIG. 1 is coupled to three leads 18, 20, 22, other lead configurations are contemplated. In other words, the number of leads coupled to IMD 16 and the locations of the leads relative to heart 12 may vary. For example, in some alternative implementations, diagnostic system 10 may include an additional lead or lead segment (not shown in FIG. 1) that deploys one or more electrodes within the left atrium, vena cava, or other vein. The additional lead may allow for alternative electrical sensing configurations that may provide improved sensing accuracy in some patients.

Figure 3:
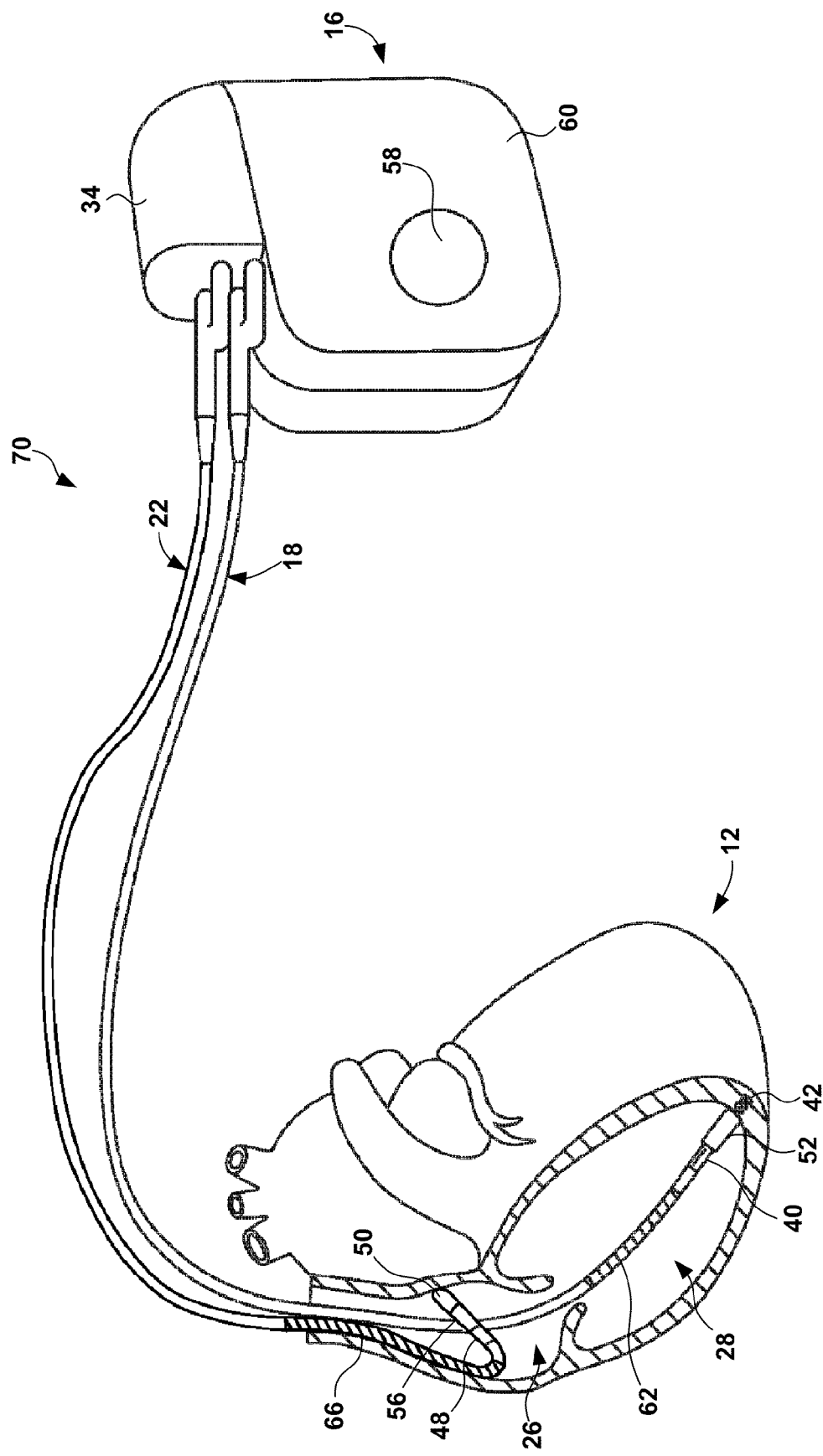
FIG. 3 is a conceptual diagram of the IMD of FIG. 1 coupled to a different configuration of leads.

FIG. 3 is a conceptual diagram illustrating another lead configuration. A system 70, similar to system 10, includes two leads 18, 22, rather than three leads. Leads 18, 22 are implanted within right ventricle 28 and right atrium 26, respectively. System 70 shown in FIG. 3 may be useful for providing defibrillation, cardioversion and pacing pulses to heart 12. The systems and methods of the present disclosure may also be implemented in system 70.

Figure 4:
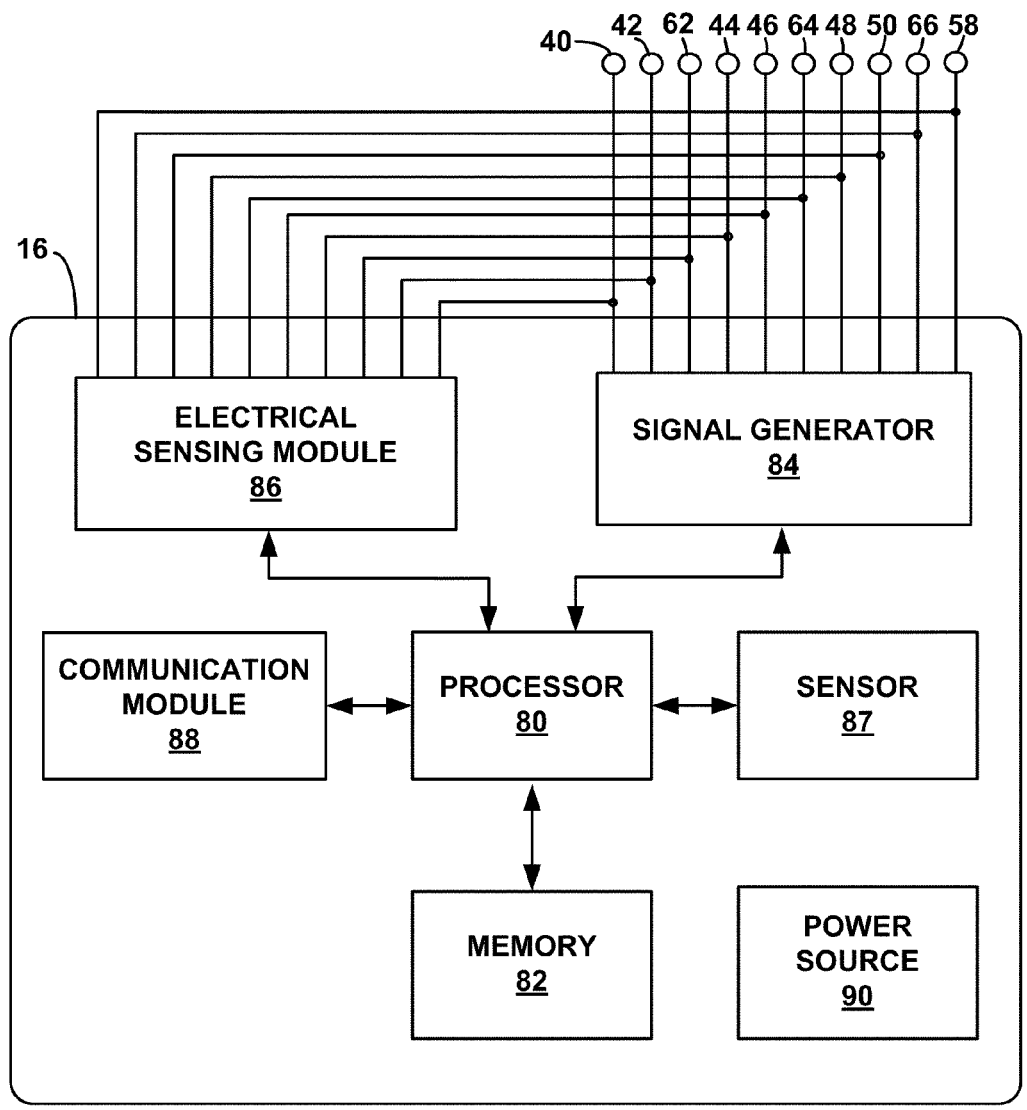
FIG. 4 is a functional block diagram illustrating an example configuration of the IMD of FIG. 1.

FIG. 4 is a functional block diagram illustrating an example configuration of IMD 16. IMD 16 includes a processor 80, memory 82, a signal generator 84, an electrical sensing module 86, a sensor 87, a communication module 88, and a power source 90. Memory 82 may include computer-readable instructions that, when executed by processor 80, cause IMD 16 and processor 80 to perform various functions attributed to IMD 16 and processor 80 herein. Memory 82 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a microcontroller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more microcontrollers, one or more DSPs, one or more ASICs, or one or more FPGAs, as well as other discrete or integrated logic circuitry. The functions attributed to processor 80 herein may be embodied as software, firmware, hardware or any combination thereof.

Signal generator 84 is electrically coupled to electrodes 40, 42, 44, 46, 48, 50, 58, 62, 64, and 66, e.g., via conductors of the respective leads 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation pulses to heart 12 via at least two electrodes 58, 62, 64, 66. Signal generator 84 may deliver pacing pulses via the ring electrodes 40, 44, 48 coupled to leads 18, 20, and 22, respectively, and/or the helical electrodes 42, 46, and 50 of leads 18, 20, and 22, respectively. In some implementations, signal generator 84 delivers pacing, cardioversion, or defibrillation stimulation in the form of electrical pulses. In other implementations, signal generator 84 may deliver one or more of these types of stimulation in the form of other signals, such as sine waves, square waves, or other substantially continuous time signals.

Processor 80 controls signal generator 84 to deliver stimulation therapy to heart 12. Processor 80 may control signal generator 84 to deliver stimulation according to a selected one or more therapy programs, which may be stored in memory 82. For example, processor 80 may control signal generator 84 to deliver electrical pulses with amplitudes, pulse widths, frequencies, or electrode polarities specified by the selected one or more therapy programs.

Processor 80 may select which of electrodes 40, 42, 44, 46, 48, 50, 58, 62, 64, and 66 delivers electrical pulses. For example, signal generator 84 may include a switch module that processor 80 may use to select, e.g., via a data/address bus, which of the available electrodes are used to deliver pacing, cardioversion, or defibrillation pulses. The switch module may include a switch array, switch matrix, multiplexer, or any other type of switching device suitable to selectively couple electrical pulses to electrodes selected by processor 80.

Electrical sensing module 86 monitors signals from at least one of electrodes 40, 42, 44, 46, 48, 50, 58, 62, 64 or 66 in order to monitor electrical activity of heart 12. Processor 80 may select which of electrodes 40, 42, 44, 46, 48, 50, 58, 62, 64, and 66 function as sense electrodes. For example, electrical sensing module 86 may include a switch module that processor 80 may use to select, e.g., via a data/address bus, which of the electrodes are used to monitor electrical activity of heart 12.

Electrical sensing module 86 may include multiple detection channels, each of which may comprise an amplifier. In response to the signals from processor 80, the switch module within the electrical sensing module 86 may couple selected electrodes to each of the detection channels.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

A portion of memory 82 may be configured as a plurality of recirculating buffers, capable of holding a series of measured intervals, which may be analyzed by processor 80 to determine whether the patient's heart 12 is presently exhibiting atrial or ventricular tachyarrhythmia. Processor 80 may detect tachyarrhythmia using any suitable tachyarrhythmia detection algorithm. In the event that processor 80 detects an atrial or ventricular tachyarrhythmia, an anti-tachyarrhythmia pacing regimen may be loaded by processor 80 and implemented using signal generator 84.

Signal generator 84 may include a high voltage charge circuit and a high voltage output circuit when IMD 16 is configured to generate and deliver defibrillation shocks to heart 12. In response to the detection of atrial or ventricular fibrillation or tachyarrhythmia requiring a cardioversion pulse, processor 80 may activate a cardioversion/defibrillation therapy using the high voltage charge circuit and the high voltage output circuit. Following delivery of the fibrillation or tachycardia therapy, processor 80 may return signal generator 84 to a cardiac pacing function and await the next successive interrupt due to pacing or the occurrence of a sensed atrial or ventricular depolarization.

IMD 16 may include one or more sensors, such as sensor 87. Sensor 87 may comprise a pressure sensor (e.g., a capacitive sensor) that senses intracardiac or other cardiovascular pressure. Sensor 87 may comprise a motion sensor. The motion sensor may be, for example, an accelerometer or piezoelectric element. Sensor 87 may also comprise a heart sound sensor, or any sensor capable of generating a signal that varies as a function of mechanical activity, e.g., contraction of heart 12. Processor 80 may receive one or more signals from sensor 87 or a plurality of sensors. Processor 80 may monitor, among other things, the mechanical activity of heart 12 based on signals from the one or more sensors.

Sensor 87 may be positioned in various locations in diagnostic system 10. For example, sensor 87 may be located within housing 60, outside of housing 60, or on or within on or more of leads 18, 20, 22. Sensor 87 may communicate with IMD 16 via wireless communication when sensor 87 is located outside of housing 60. In some implementations, sensor 87 may be external (i.e., not implanted).

Communication module 88 includes any suitable hardware, firmware, software or any combination thereof for communicating with another device, such as programmer 24 and/or patient monitor 25. Under the control of processor 80, communication module 88 may receive downlink telemetry from and send uplink telemetry to programmer 24 and/or patient monitor 25 with the aid of an antenna (not shown), which may be internal and/or external. Processor 80 may provide the data to be uplinked to programmer 24 and/or patient monitor 25 and the control signals for telemetry circuitry within communication module 88, e.g., via an address/data bus.

Processor 80 may transmit atrial and ventricular heart signals (e.g., EGMs) detected by atrial and ventricular sense amplifier circuits within electrical sensing module 86 to programmer 24 and/or patient monitor 25. Additionally, programmer 24 and/or patient monitor 25 may interrogate IMD 16 to receive the EGMs. Processor 80 may provide stored and/or real-time EGMs to programmer 24 and/or patient monitor 25 via communication module 88.

Processor 80 may store the EGMs in memory 82, and retrieve the stored EGMs from memory 82. Processor 80 may also generate marker channel data and store marker channel data in memory 82. Marker channel data may indicate the occurrence and timing of sensing, diagnosis, and therapy events, e.g., P-waves, R-waves, tachyarrhythmia (e.g., tachycardia or fibrillation), pacing pulses, anti-tachycardia pacing (ATP), cardioversion shocks, or defibrillation shocks, detected, diagnosed, or undertaken by IMD 16. Programmer 24 and/or patient monitor 25 may interrogate IMD 16, via communication module 88, to receive the marker channel data. Processor 80 may also provide the marker channel data to programmer 24 and/or patient monitor 25 in real-time via communication module 88, e.g., when the marker channel data is generated.

Processor 80 may store EGMs corresponding to physiological episodes, such as tachyarrhythmias, in memory 82. For example, processor 80 may store EGMs for atrial and ventricular tachycardia and fibrillation episodes, in response to the detection of the tachycardia or fibrillation. Processor 80 may also store EGMs corresponding to nonsustained tachycardia (NST) in memory 82 in response to detection of the NST using any suitable NST detection technique. Programmer 24 and/or patient monitor 25 may interrogate IMD 16, via communication module 88, to receive the stored EGMs.

Processor 80 may also store parametric data in memory 82. Parametric data may include, for example, impedance measurements, trends of impedance measurements, or statistical or other processed values determined based on impedance measurements. Parametric data may also include the programmed settings/algorithms of IMD 16, e.g., at the time an episode was detected/treated as described herein. Other parametric data may include data indicating the current status of power source 90 of IMD 16. Programmer 24 and/or patient monitor 25 may interrogate IMD 16, via communication module 88, to receive the parametric data. Processor 80 may also provide the parametric data to programmer 24 and/or patient monitor 25 in real-time via the communication module 88, e.g., when the parametric data is measured.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 5:
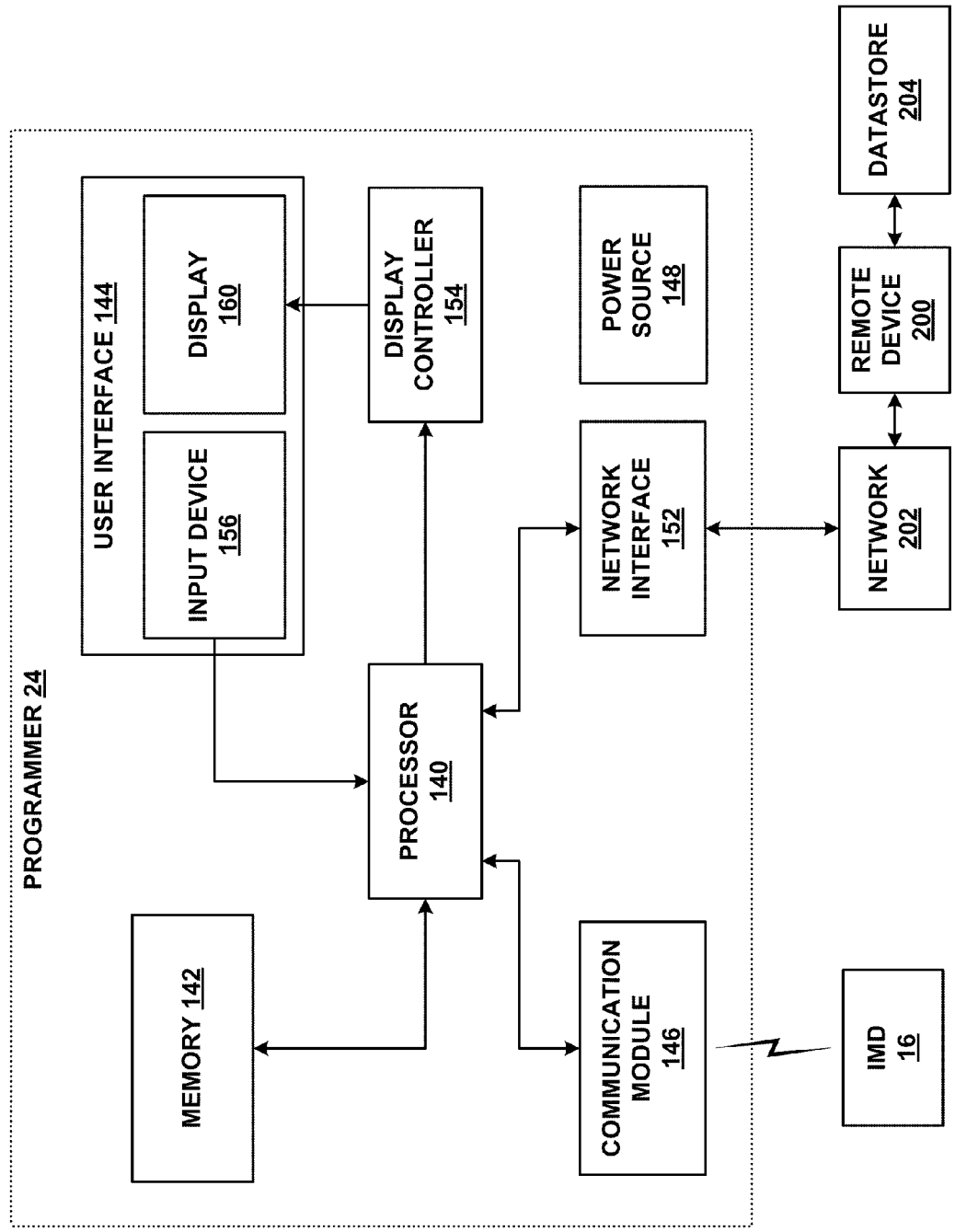
FIG. 5 is a functional block diagram of an example programmer.

FIG. 5 is an example functional block diagram of programmer 24. Programmer 24 includes a processor 140, memory 142, a user interface 144, a communication module 146, a power source 148, a network interface 152, and a display controller 154. Programmer 24 may be a dedicated hardware device with dedicated software for communicating with IMD 16. For example, programmer 24 may be a dedicated hardware device that programs operational parameters of IMD 16 and/or receives data from IMD 16. Alternatively, programmer 24 may be an off-the-shelf computing device, such as a desktop or laptop computer, running an application that enables programmer 24 to communicate with IMD 16 (i.e., receive data from IMD 16 and/or program IMD 16). Accordingly, programmer 24 represents any computing device capable of performing the functions attributed to programmer 24 in the present disclosure.

The user interacts with programmer 24 using user interface 144. User interface 144 includes an input device 156 and a display 160 (e.g., an LCD display). The user enters data into programmer 24 using input device 156. Input device 156 may include various devices for entering data. Input device 156 may include a keypad, for example, an alphanumeric keypad or a reduced set of keys associated with particular functions of programmer 24. Input device 156 may also include a freehand peripheral input device such as a mouse, a stylus, and a touchscreen.

Network interface 152 may communicate with a remote device 200 via a network 202. Remote device 200 may include, for example, a general purpose computing device such as an off-the-shelf desktop/laptop computer or server computer configured to communicate with programmer 24 via network 202. Network 202 may include various types of networks, such as a wide area network (WAN) and/or the Internet, for example. Although network 202 may represent a long range network (e.g., Internet or WAN), in some implementations, network 202 may be a shorter range network, such as a local area network (LAN).

Processor 140 can take the form of one or more microprocessors, DSPs, ASICs, FPGAs, programmable logic circuitry, or the like, and the functions attributed to processor 140 herein may be embodied as hardware, firmware, software or any combination thereof. Processor 140 of programmer 24 may provide any of the functionality ascribed herein, or otherwise perform any of the methods described herein.

Memory 142 may store instructions that cause processor 140 to provide the functionality ascribed to programmer 24 herein. Memory 142 may also store information used by processor 140 to provide the functionality ascribed to programmer 24 herein. Memory 142 may include any fixed or removable magnetic, optical, or electrical media, such as random access memory (RAM), read-only memory (ROM), compact-disc ROM (CD-ROM), hard or floppy magnetic disks, electrically erasable programmable ROM (EEPROM), or the like. Memory 142 may also store information that controls therapy delivery by IMD 16.

Programmer 24 may store data in a datastore 204. For example, processor 140 may transfer data to remote device 200, which then transfers the data to datastore 204. Accordingly, remote device 200 may be a server that communicates with programmer 24 to store data from programmer 24 in datastore 204 and retrieve data from datastore 204 for use by programmer 24. Datastore 204 may include any type of computer data storage or computer memory for storing data received from remote device 200. For example, datastore 204 may include magnetic storage media (e.g., hard disk drives), optical media (e.g., digital versatile disc drives), and/or solid state memory (e.g., dynamic random access memory or EEPROM).

In some implementations, remote device 200 and datastore 204 may include network technology and functionality similar to that provided by the Medtronic CareLink® Network developed by Medtronic, Inc., of Minneapolis, Minn. The data stored in datastore 204 may include, for example, EGMs, marker channel data, parametric data, or other sensed physiological parameters of patient 14, such as intracardiac or intravascular pressure, activity, posture, respiration, or thoracic impedance. In other implementations, remote device 200 and datastore 204 may represent or interface with a system configured to store electronic medical records, which may additionally or alternatively include other waveforms or medical information for patient 14.

Programmer 24 may communicate wirelessly with IMD 16, such as using RF communication or proximal inductive interaction. This wireless communication is possible through the use of communication module 146, which may be coupled to an internal antenna or an external antenna. For example, an external antenna may be included in a programming head (not shown) that is coupled to programmer 24. The programming head may be placed over heart 12 (i.e., IMD 16), as described above with reference to FIG. 1 to communicate with IMD 16. Communication module 146 may include similar functionality as communication module 88 of IMD 16.

Communication module 146 may also be configured to communicate with another computing device via wireless communication techniques. Examples of local wireless communication techniques may include RF communication according to the Institute of Electrical and Electronics Engineers (IEEE) 802.11, Bluetooth specification sets, infrared communication, e.g., according to the IrDA standard, or other standard or proprietary telemetry protocols.

Although programmer 24 is described as including communication module 146 that wirelessly receives EGMs and other data from IMD 16, in other implementations, programmer 24 may include additional or alternative interfaces that receive additional or alternative waveforms. For example, programmer 24 may include an interface that receives, electrocardiogram (ECG) waveforms, or neurological waveforms, such as electroencephalography (EEG) waveforms. The systems and methods of the present disclosure may also be applicable to other types of acquired waveforms or other data instead of or in addition to EGMs, ECG, and EEG waveforms.

Display controller 154 receives data from processor 140 and generates output images on display 160. In other words, display controller 154 is configured to display information on the display 160. For example, display controller 154 may display EGMs on display 160.

Power source 148 delivers operating power to the components of programmer 24. Power source 148 may include a battery and/or adapter for connection to an alternating current (AC) wall socket.

Figure 6:
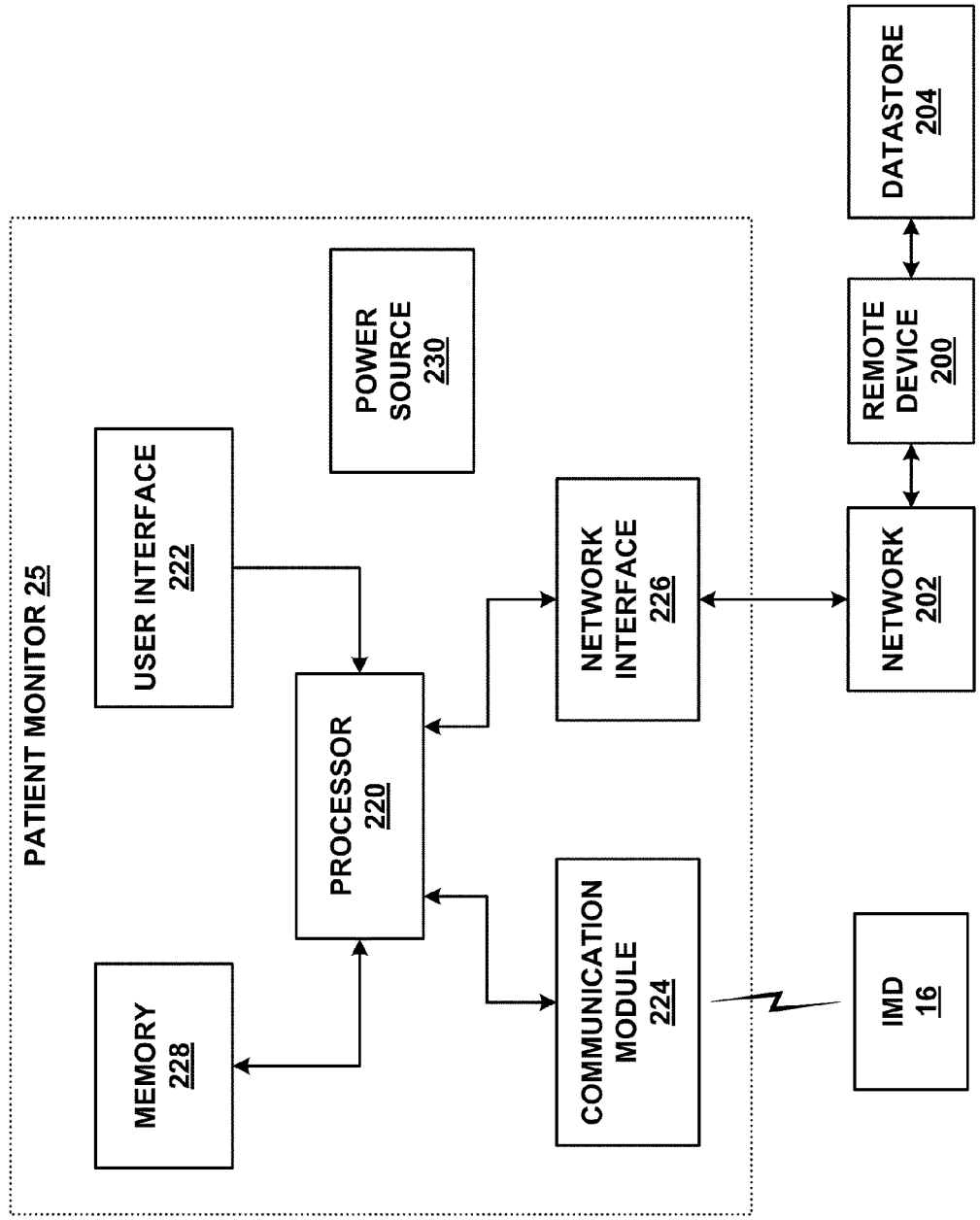
FIG. 6 is a functional block diagram of an example patient monitor.

FIG. 6 shows an example patient monitor 25. Patient monitor 25 may be a device that the patient uses to transfer data from IMD 16 to a clinic or to remote device 200 (e.g., the CareLink Network). For example, patient monitor 25 may be a device that patient 14 keeps in their home in order to transfer data from IMD 16 to remote device 200 while at home. Patient monitor 25 may represent a commercially available product, such as a Medtronic CareLink® Monitor developed by Medtronic, Inc., of Minneapolis, Minn.

Patient monitor 25 may include a processor 220, a user interface 222, a communication module 224, a network interface 226, memory 228, and a power source 230. The components of patient monitor 25 may function similarly to those of programmer 24. Power source 230 delivers operating power to the components of patient monitor 25.

The user may interact with patient monitor 25 using user interface 222. User interface 222 may include an input device and a display (e.g., an LCD display). The user may enter data into user interface 222 using a keypad, for example, an alphanumeric keypad or a reduced set of keys associated with particular functions of patient monitor 25. User interface 222 may also include a freehand peripheral input device such as a mouse, a stylus, and a touchscreen. Although illustrated as including user interface 222, in other examples patient monitor 25 need not include a user interface.

Patient monitor 25 may communicate with remote device 200 using network interface 226. In some implementations, network interface 226 may include a phone line interface (e.g., a modem) for connecting to network 202 through a phone line connection.

Processor 220 can take the form of one or more microprocessors, microcontrollers, DSPs, ASICs, FPGAs, programmable logic circuitry, or the like, and the functions attributed to processor 220 herein may be embodied as hardware, firmware, software or any combination thereof. Processor 220 of patient monitor 25 may provide any of the functionality ascribed herein, or otherwise perform any of the methods described herein.

Memory 228 may store instructions that cause processor 220 to provide the functionality ascribed to patient monitor 25 herein. Memory 228 may also store information used by processor 220 to provide the functionality ascribed to patient monitor 25 herein. Memory 228 may include any fixed or removable magnetic, optical, or electrical media, such as RAM, ROM, CD-ROM, hard or floppy magnetic disks, EEPROM, or the like.

Patient monitor 25 may send data to a clinic and/or datastore 204. For example, patient monitor 25 may transfer data to remote device 200, which may then transfer the data to the clinic and/or datastore 204.

Patient monitor 25 may communicate wirelessly with IMD 16, such as using RF communication or proximal inductive interaction. This wireless communication is possible through the use of communication module 224, which may be coupled to an internal antenna or an external antenna. For example, an external antenna may be included in a monitoring head (not shown) that is coupled to patient monitor 25. The monitoring head may be placed over IMD 16 to communicate with IMD 16. Communication module 224 may include similar functionality as communication module 146 of programmer 25 and communication module 88 of IMD 16.

Patient 14 may operate patient monitor 25 in the following manner. Patient 14 may power patient monitor 25 on, e.g., using a power button on user interface 222. Next, patient 14 may place the programming head over IMD 16. Patient monitor 25 may then communicate with IMD 16 to read data from IMD 16. In other examples, patient monitor 25 need not utilize a programming head to wirelessly communicate with IMD 16, or may automatically communicate with IMD 16.

Data read from IMD 16 by patient monitor 25 may include, for example, EGMs, marker channel data, parametric data, or other sensed physiological parameters of patient 14, such as intracardiac or intravascular pressure, activity, posture, respiration, or thoracic impedance. Patient monitor 25 may then send the data received from IMD 16 to remote device 200 through network 202 (e.g., over a phone line). Remote device 200 may store received data in datastore 204 and/or send the data to the patient's clinic for review.

In addition to, or alternative to, using programmer 24 and patient monitor 25, patient 14 may use another communication device to transmit data to datastore 204. For example, patient 14 may use a cellular phone to transmit data to remote device 200 through network 202, then remote device 200 may store the data received from the cellular phone in datastore 204.

Figure 7:
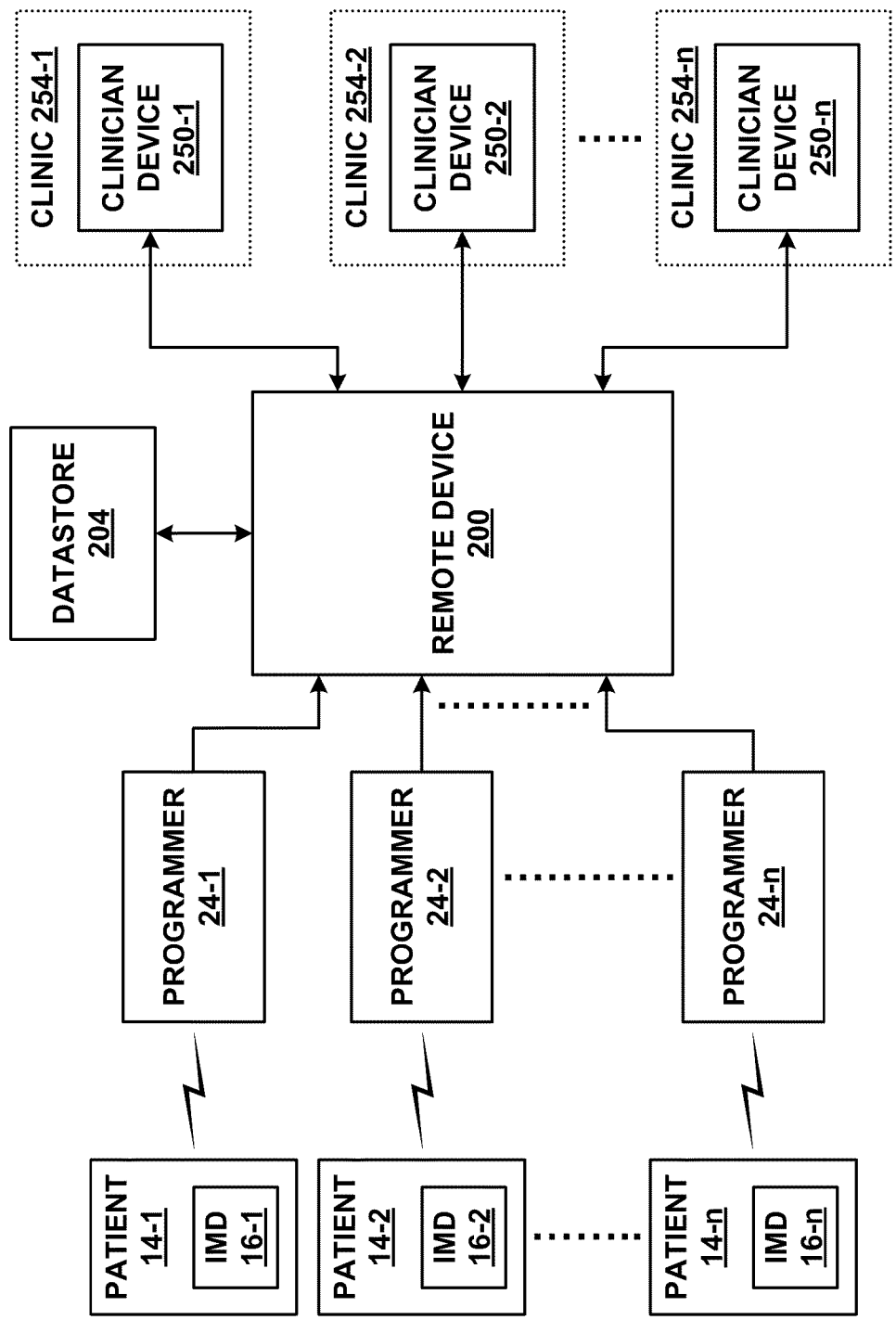
FIG. 7 is a block diagram illustrating communication within an example system that includes a plurality of the IMDs and a remote device.

FIG. 7 illustrates transmissions from a plurality of IMDs to remote device 200. The IMDs 16-1, 16-2, . . . , and 16-$n$ (collectively "IMDs 16") are implanted in patients 14-1, 14-2, . . . , and 14-$n$ (collectively "patients 14"). The programmers 24-1, 24-2, . . . , and 24-$n$ (collectively "programmers 24") may represent programmers 24 used by patients 14 to transmit data from IMDs 16 to remote device 200. Although programmers 24 are illustrated, any or each of programmers 24 may be replaced with a patient monitor 25. Accordingly, data may be transmitted from IMDs 16 to remote device 200 using a programmer 24 (e.g., in a clinician's office) and/or using patient monitor 25 (e.g., at a patient's home).

Remote device 200 may be a computing device (e.g., a server) that is connected to programmers 24 through a network. Since patients 14 may be located in various clinics or residences apart from one another, e.g., across the United States or across the globe, programmers 24 may connect to remote device 200 through various long range networks, such as a WAN and/or the Internet. Although remote device 200 is described as being connected to programmers 24 through a long range network, in some implementations, remote device 200 may be connected to programmers 24 through a shorter range network, such as a LAN.

Remote device 200 may include, for example, a general purpose computing device. Remote device 200, and modules included in remote device 200, may be implemented, at least in part, in hardware, software, firmware or any combination thereof. For example, various aspects of remote device 200 may be implemented within one or more processors, including one or more microprocessors, DSPs, ASICs, FPGAs, or any other equivalent integrated or discrete logic circuitry, as well as any combinations of such components. When implemented in software, the functionality ascribed to remote device 200 may be embodied as instructions on a computer-readable medium such as RAM, ROM, NVRAM, EEPROM, FLASH memory, magnetic data storage media, optical data storage media, or the like. The instructions may be executed to support one or more aspects of the functionality of remote device 200 described in this disclosure.

Remote device 200 may store data received from programmers 24 (i.e., IMDs 16) in datastore 204 and may also retrieve stored data from datastore 204. Data stored in and retrieved from datastore 204 may include, for example, EGMs, marker channel data, parametric data, or other sensed physiological parameters of patient 14, such as intracardiac or intravascular pressure, activity, posture, respiration, or thoracic impedance.

Datastore 204 may be accessed by one or more clinician devices 250-1, 250-2, . . . , and 250-$n$ (collectively "clinician devices 250"). Clinician devices 250 may represent any general computing device used (e.g., by clinicians) to communicate with remote device 200, such as general purpose desktop/laptop computers.

Each of clinician devices 250 of FIG. 7 are associated with a different one of the clinics 254-1, 254-2, . . . , 254-$n$ (collectively "clinics 254"). Clinics 254 may represent any health facility that is devoted to the care of patients 14. For example, clinics 254 may represent smaller health facilities, e.g., that serve local communities, or larger hospitals. Clinics 254 may be operated by one or more clinicians that are associated with IMDs 16. In other words, clinics 254 may be operated by one or more clinicians that have implanted IMDs 16 or provide follow-up services associated with the IMDs 16. Accordingly, each of clinician devices 250 may represent a general computing device that may be used by a clinician to access datastore 204 to retrieve data regarding IMDs 16 with which the clinician is associated.

Generally, clinician devices 250 may represent computing devices that are remotely located from one another. For example, each clinician device 250 may represent a different computing device located at a different clinic, for example, across the United States, or across the globe. Since clinics 254 may be located remotely from one another, clinician devices 250 may connect to remote device 200 through various long range networks such as the Internet, a WAN, etc. Although clinician devices 250 are described as being connected to remote device 200 through a long range network, in some implementations, clinician devices 250 may be connected to remote device 200 through a shorter range network, such as a LAN.

The clinician may view data retrieved by remote device 200 from datastore 204 using a clinician device 250. Clinician device 250 and/or remote device 200 may analyze data from datastore 204, then clinician device 250 and/or remote device 200 may format and present the data to the clinician on a display of clinician device 250. A presentation of data on the display of clinician device 250 may generally be referred to as a "dashboard." Data presented on the dashboard may be used to assist the clinician in making informed decisions regarding treatment of patients 14. For example, a dashboard that displays data relating to operation of the IMDs 16 may allow the clinician to make informed decisions regarding programming of the IMDs 16 and selection of a type of IMD to implant in the future. In one example, the dashboard can inform a clinician of the effectiveness of their practice by displaying an overview of IMD therapy performance for the patients associated with that practice as compared to IMD therapy performance data from other practices or on a national level. Example dashboards and corresponding data relating to IMDs 16 are illustrated in FIGS. 11-14. Although the dashboard is described as being displayed on a display of clinician device 250, the dashboard may also be printed out as a hard copy using clinician device 250.

As described herein, the dashboard may include a representation of data collected from IMDs 16 implanted in patients 14. For example, the dashboard may present data relating to EGMs, marker channel data, parametric data, or other sensed physiological parameters of patient 14, such as intracardiac or intravascular pressure, activity, posture, respiration, or thoracic impedance. The dashboard may also present data relating to a number of shocked episodes associated with all patients 14, events that precipitated the shocked episodes, and whether the shocked episodes were appropriate or inappropriate. Shocked episodes may include events in which an IMD delivers one or more consecutive shocks to a patient over a period of time (e.g., over a period of seconds) in response to detection of one or more VT/VF events. Shocked episodes may include shocks that were delivered appropriately in response to detection of one or more consecutive VT/VF events, or inappropriately, in response to an inappropriately characterized SVT or in response to oversensing or undersensing. Additionally, in some examples, the dashboard may also present data relating to whether shocked episodes were delivered in response to detection of atrial fibrillation, sinus tachycardia, atrial flutter, or atrial tachycardia, and whether the shocked episodes were delivered appropriately or inappropriately in response to these detections. Typically, multiple consecutive shocks within a shocked episode arise for similar reasons. For example, if a first shock is delivered in response to detection of a VT/VF event, whether appropriate or inappropriate, subsequent shocks are typically delivered in response to the same event or type of event (i.e., VT/VF events). The dashboard may numerically and graphically present the information to the clinician, e.g., using charts and graphs.

The clinician may enter selection parameters in clinician device 250 to control what information is generated on the dashboard. In general, the selection parameters entered into clinician device 250 define the information the clinician is interested in reviewing on the dashboard. The selection parameters may indicate a type of data the clinician is interested in viewing, for example, data regarding a number shocked episodes associated with patients 14. The selection parameters may also include a type of comparison to be made with the data, for example, a comparison of the number of shocked episodes associated with patients of the clinician's clinic to all other clinics in datastore 204. Clinician device 250 may generate a request to remote device 200 that indicates the type of data the clinician is interested in viewing and the type of comparison to be made with the data.

Remote device 200 retrieves data from datastore 204 based on the request from clinician device 250. Remote device 200 then processes the data retrieved from datastore 204. Remote device 200 then sends the processed data to clinician device 250 to be displayed to the clinician who requested the data. For example, when the clinician enters selection parameters that indicate the number shocked episodes associated with all IMDs 16, remote device 200 may determine the number of shocked episodes associated with all IMDs 16 in datastore 204. Remote device 200 may then send the number to clinician device 250 for display on a dashboard. As a further example, when the selection parameters further indicate a desire by the clinician to view a comparison of the number of shocked episodes associated with a specific one of clinics 254 to all other clinics, remote device 200 may determine a number of shocked episodes associated with the specific clinic and a number associated with all clinics, then return the two numbers to the clinician device 250. The clinician device 250 may then display the comparison of the two numbers on a dashboard in a numerical or graphical representation. Selection parameters, retrieval of data from datastore 204, processing of data, and display of the data on a dashboard is described hereinafter.

Figure 8:
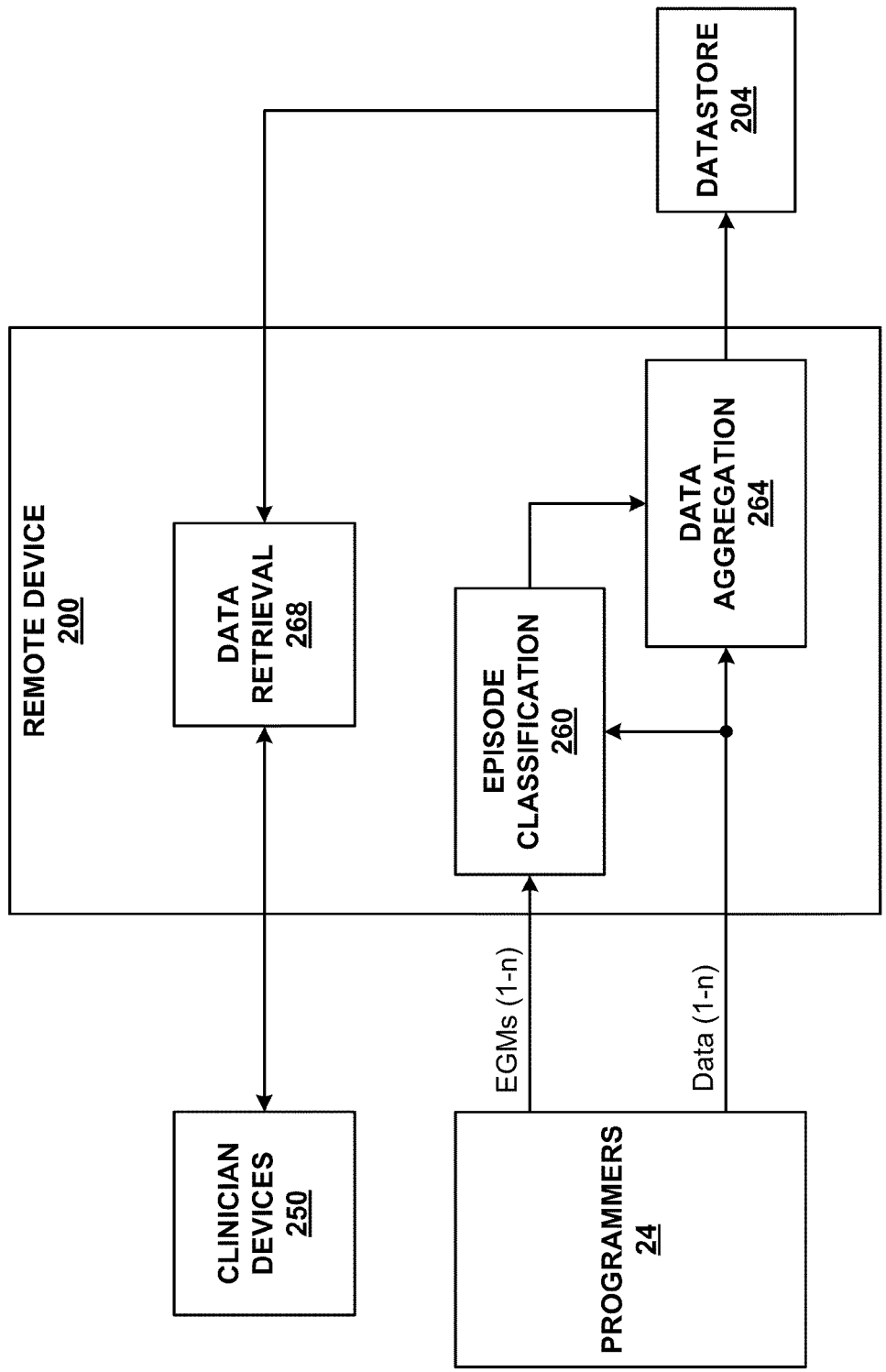
FIG. 8 is a functional block diagram of an example remote device.

FIG. 8 shows an example implementation of remote device 200. Remote device 200 includes an episode classification module 260, a data aggregation module 264, and a data retrieval module 268. Episode classification module 260 receives EGMs from programmers 24. EGMs received by episode classification module 260 may have been stored for a variety of reasons by IMDs 16. For example, the EGMs may have been stored if the EGMs precipitated a defibrillation shock or other therapy by IMD 16. In other words, IMD 16 may have stored the EGMs if IMD 16 determined that the EGMs indicated a ventricular tachycardia (VT) or a ventricular fibrillation (VF) and the IMD 16 delivered a defibrillation shock or other therapy, e.g., cardioversion shock or antitachycardia pacing, in response to the detection of the VT or VF. Episode classification module 260 may also receive other data from IMD 16, such as marker channel data.

Typically, an IMD may deliver one shock to successfully treat a VT/VF event, however, some VT/VF events may recur subsequent to a single shock. VT/VF that recurs subsequent to a shock may require additional shocks for successful treatment. Accordingly, in order to provide sufficient therapy, an IMD may shock a patient more than one time in response to detection of more than one VT/VF event. The EGMs transmitted to remote device 200 may each include one or more consecutive shocks due to consecutive detection of VT/VF events, detection of SVT events, and detection of noise and oversensing/undersensing events. The EGMs and other data received from IMDs 16 that are associated with an episode that resulted in delivery of one or more defibrillation shocks or other electrical therapy may be referred to as associated with shocked episodes.

EGMs sent from the n programmers 24 are labeled as EGMs (1-n) in FIG. 8. Each of the EGMs associated with delivery of one or more defibrillation shocks may correspond to one shocked episode. In some cases, EGMs sent from the n programmers may each be associated with multiple shocks, e.g., in the case where the IMD from which the EGM was received applied a plurality of shocks in response to detection of one or more VT/VF events.

Episode classification module 260 may determine whether the EGMs are associated with a defibrillation shock or other therapy, e.g., based on marker channel data associated with the EGM waveform. For example, the marker channel data may indicate when a defibrillation shock was delivered. Episode classification module 260 analyzes the received EGMs for episodes that precipitated defibrillation shocks or other therapies and characterizes the EGMs, i.e., characterizes the shocked episodes. For example, episode classification module 260 may characterize a shocked episode as resulting from one of VF, VT, supra-ventricular tachycardia (SVT), oversensing, or undersensing. For example, oversensing may include sensing of extraneous potentials such as T waves, muscle potentials, ambient noise, noise due to lead integrity issues, etc. Undersensing may include a failure of an IMD to sense P or R waves.

Episode classification module 260 may characterize the shocked episodes as indicating VF, VT, SVT, or oversensing using various techniques. For example, episode classification module 260 may characterize the shocked episodes based on at least one of a ratio of atrial sensed events to ventricular sensed events, a rate of intervals detected, or a correlation between EGM morphology and stored EGM templates from the patient. According to an example of the present disclosure, shocked episodes may be characterized using techniques described in U.S. patent application Ser. No. 11/564,120, filed Nov. 28, 2006, titled "Method and Apparatus for Post-Processing of Episodes Detected by a Medical Device," which is incorporated herein by reference in it's entirety.

Additionally, episode classification module 260 may determine whether IMDs 16 provided defibrillation shocks or other therapy that were appropriate or inappropriate based on the characterization of the shocked episodes. Generally, a shocked episode was appropriate if defibrillation shocks were delivered during the shocked episode in a situation where the defibrillation shocks were required due to a potentially life threatening arrhythmia. Accordingly, episode classification module 260 may determine that a shocked episode was appropriate when episode classification module 260 characterizes the episode that precipitated one or more shocks as a VT or VF, since VT and VF may be life threatening arrhythmias that may require a defibrillation shock for correction.

Generally, a shocked episode may not have been appropriate (i.e., inappropriate) if defibrillation shocks delivered during the shocked episode were not required to be delivered by IMD 16, but may have been delivered by IMD 16 in error, based on detection of a SVT, based on oversensing of cardiac events, or based on sensing non-cardiac events, such as lead integrity issues that give rise to lead noise. Accordingly, episode classification module 260 may determine that a shocked episode was inappropriate when episode classification module 260 characterizes the EGM and/or other data of the shocked episode as indicative of SVT, or determines that IMD 16 delivered one or more shocks due to oversensing, or based on non-cardiac events such as lead noise. In some examples, episode classification module 260 may characterize a shocked episode as inappropriate if the EGM associated with the shocked episode indicates atrial fibrillation, sinus tachycardia, atrial flutter, or atrial tachycardia.

Figure 9:
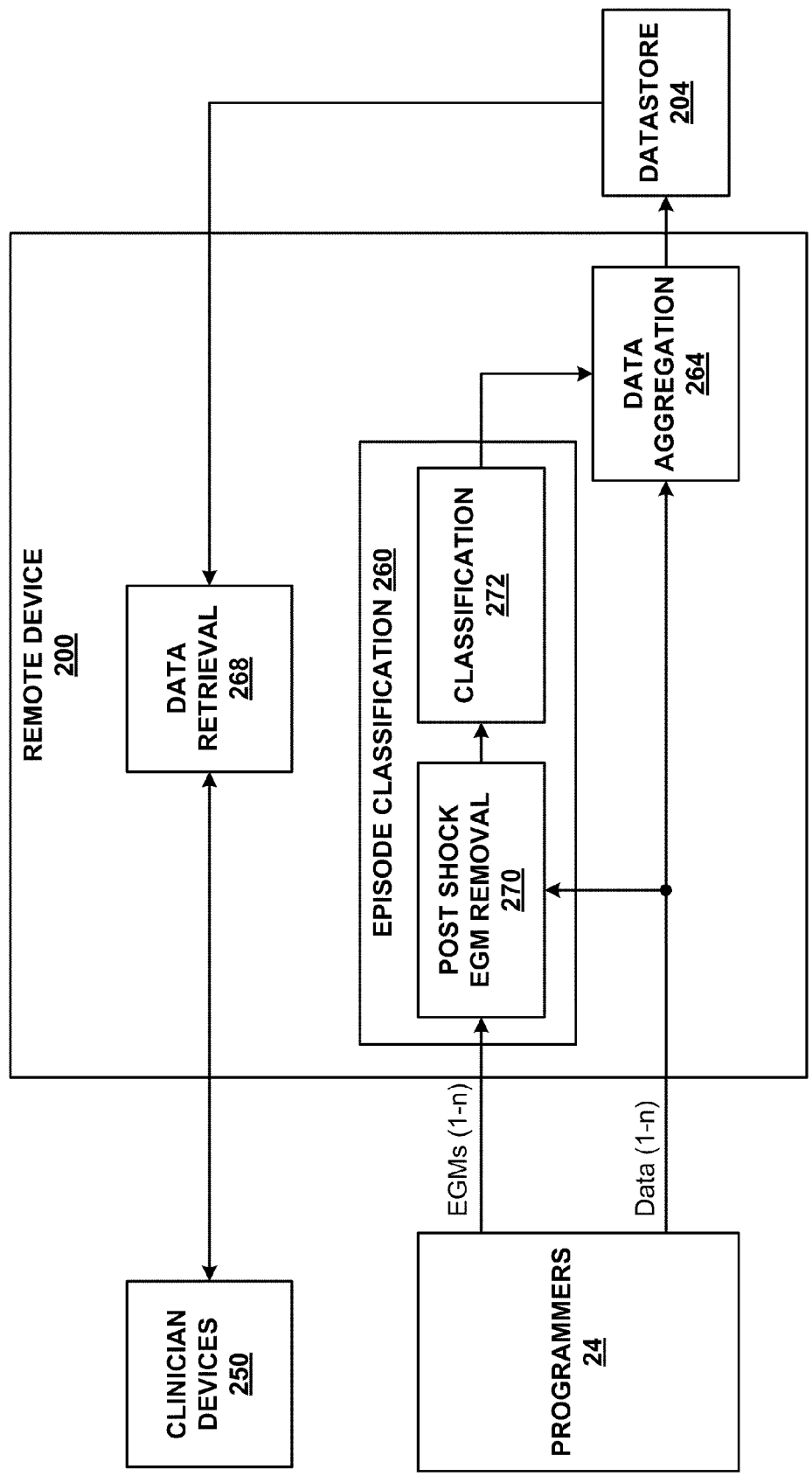
FIG. 9 is a functional block diagram of an example implementation of the remote device of FIG. 8.

In addition to receiving EGMs (1-n), episode classification module 260 may receive other data (e.g., represented as Data (1-n) in FIGS. 8-9) such as marker channel data, parametric data (e.g., programmed settings/algorithms of IMD 16 corresponding to an episode), or other sensed physiological parameters of patient 14, such as intracardiac or intravascular pressure, activity, posture, respiration, or thoracic impedance. Episode classification module 260 may characterize the shocked episodes as either appropriate or inappropriate based on the other data received in addition to, or in lieu of, the received EGMs.

Episode classification module 260 may characterize a shocked episode as inappropriate if the shocked episode indicates the presence of non-cardiac events, such as lead noise. Episode classification module 260 may determine that a shocked episode resulted from lead noise using a variety of techniques. For example, episode classification module 260 may determine that a shocked episode resulted from lead noise based on a lead impedance value that indicates a lead integrity issue, e.g., a high lead impedance value that indicates a lead fracture. Additionally, episode classification module 260 may detect a lead integrity issue based on the presence of short intervals in an episode, e.g., a number of detected short intervals within a period of time. Furthermore, episode classification module 260 may detect a lead integrity issue based on the presence of non-sustained episodes, e.g., a number of non-sustained VT episodes over a period of time. Example techniques for detecting oversensing, undersensing, and lead integrity issues are described in U.S. Patent Application Publication No. 2004/0015197 by Gunderson, U.S. Patent Application Publication No. 2004/0064161 by Gunderson et al., U.S. Patent No. 2005/0137636 by Gunderson et al., U.S. Patent Application Publication No. 2006/0116732 by Gunderson et al., U.S. Patent Application Publication No. 2006/0116733 by Gunderson, and U.S. Patent Application Publication No. 2006/0235476 by Gunderson et al. U.S. Patent Application Publication Nos. 2004/0015197, 2004/0064161, 2005/0137636, 2006/0116732, 2006/0116733, and 2006/0235476 are incorporated herein by reference in their entirety.

Although episode classification module 260 is described as determining whether shocked episodes were appropriate/inappropriate, episode classification module 260 may also determine whether therapy was inappropriately withheld. In other words, episode classification module 260 may determine whether therapy was not delivered when therapy should have been delivered. For example, episode classification module 260 may determine that therapy was inappropriately withheld when episode classification module 260 determines that a defibrillation shock or ATP was not provided during VT. As a further example, episode classification module 260 may determine that therapy was inappropriately withheld when cardioversion therapy or ATP was not provided during a SVT.

Episode classification module 260 may determine an accuracy value associated with each characterization of a shocked episode as VF, VT, SVT, or oversensing. The accuracy value may indicate an accuracy of the characterization, and accordingly, the extent to which the determination may be relied on by a clinician. For example, a high accuracy may indicate that the characterization is reliable, while a low accuracy may indicate that the characterization is less reliable.

In some implementations, episode classification module 260 may classify a shocked episode as "indeterminate" to indicate that the shocked episode may not be accurately classified. For example, episode classification module 260 may classify the shocked episode as indeterminate when an accuracy value associated with the shocked episode is less than a threshold value.

Actual visual inspection of shocked episodes by a clinician may include a certain amount of uncertainty as to whether a shocked episode indicates VF, VT, SVT, oversensing, or undersensing. The accuracy value may be conceptualized as a simulation of this uncertainty associated with characterizations made by the clinician. Accordingly, the accuracy value may be a parameter that accounts for the reality that not all shocked episodes may be confidently characterized by a clinician or algorithm. The clinician may set a selection parameter that indicates their desire to view accuracy values corresponding to shocked episodes in the dashboard.

Figure 10:
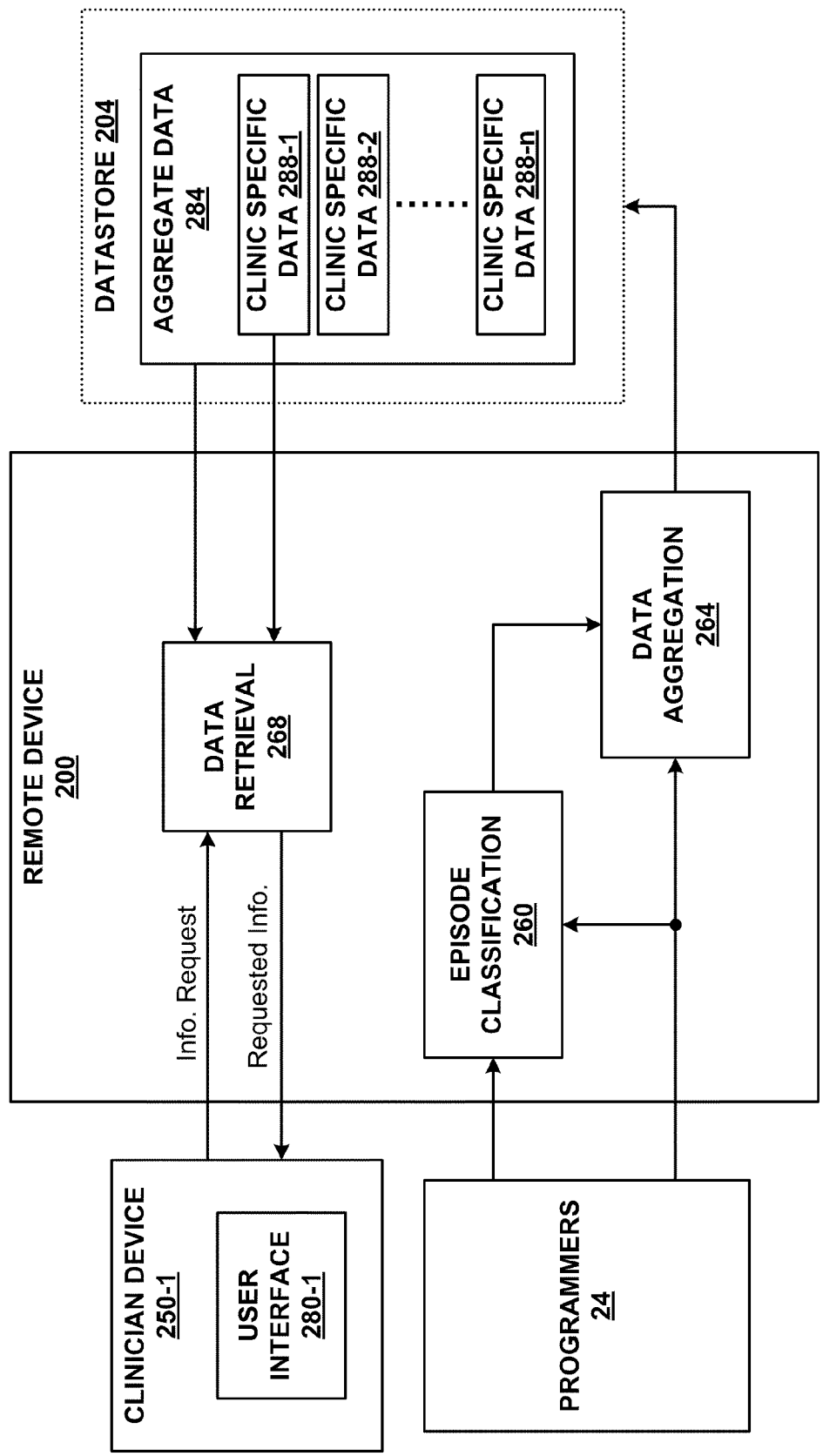
FIG. 10 is a block diagram illustrating request and receipt of information at a single clinic using a clinician device.

Although episode classification module 260 is illustrated in FIGS. 8-10 as receiving EGMs and other data directly from programmers 24, in other implementations, episode classification module 260 may retrieve EGMs and other data from datastore 204 for classification.

An example implementation of episode classification module 260 is shown in FIG. 9. Episode classification module 260 may include a post shock EGM removal module 270 and a classification module 272. The EGMs (1-*n*) received from programmers 24 may include a segment of waveform that occurs prior to an initial defibrillation shock and a segment of waveform that occurs during and after the initial defibrillation shock. Post shock EGM removal module 270 may remove the segment of the waveform that occurs during and after the initial defibrillation shock since the defibrillation shock may change the characteristics of the EGM waveform, which may prevent classification of the shocked episode. Additionally, since interest in whether the defibrillation shock was appropriate/inappropriate may be based on data prior to the initial defibrillation shock, the segment of waveform that occurs at the time of the initial shock and after the initial shock may not be relevant to classification of the shocked episode. In some examples, post shock EGM removal module 270 may determine which portion of the EGMs to remove based on marker channel data that indicates when a defibrillation shock was delivered. Classification module 272 receives the EGMs that have had segments removed after the defibrillation shock. Classification module 272 may characterize the shocked episodes and determine whether the shocked episodes were appropriate or inappropriate based on the EGMs.

In some implementations, post shock EGM removal module 270 may not be included in episode classification module 260. Accordingly, in these implementations, the segment of the waveform that occurs during and after the initial defibrillation shock may not be removed from the EGM. In these implementations, classification module 272 may analyze the segment of the waveform that occurs during and after the defibrillation shock since analysis of the way the heart responded to the delivered shock may be useful in characterizing whether the shocked episode was appropriate/inappropriate.

Data aggregation module 264 may store data received from episode classification module 260 in datastore 204. For example, data aggregation module 264 may store data in datastore 204 that indicates a number of shocked episodes associated with each of the IMDs 16, a number of appropriate shocked episodes associated with each of the IMDs 16, a number of inappropriate shocked episodes associated with each of IMDs 16, etc. Additionally, data aggregation module 264 may store data in datasore 204 that indicates a cause of the shocked episode (e.g, VT/VF, SVT, noise, oversensing, undersensing etc.). Also, data aggregation module 264 may store additional data from the IMDs 16 in datastore 204, such as, EGMs, marker channel data, parametric data, or other sensed physiological parameters of patient 14, such as intracardiac or intravascular pressure, activity, posture, respiration, or thoracic impedance. The additional data is represented in FIGS. 8-9 as Data (1-*n*).

Data aggregation module 264 may store data in datastore 204 so that the stored data may be searched and retrieved from datastore 204 by data retrieval module 268. Data retrieval module 268 may search and retrieve data from datastore 204 based on the selection parameters entered by the clinician and received from clinician device 250.

In one implementation, data aggregation module 264 may store data based on a clinic 254 from which the data was received so that data retrieval module 268 may retrieve data from datastore 204 based on the clinic from which the data was received. To see data relating to a specific clinic, the clinician may set the selection parameter to indicate that specific clinic, and data retrieval module 268 may retrieve data relevant to that specific clinic when the data is stored based on a clinic. For example, the clinician of clinic 254-1 may set a selection parameter indicating clinic 254-1 and data retrieval module 268 may retrieve data from datastore 204 that is relevant to clinic 254-1 for display to the clinician, such as a number of shocked episodes associated with IMDs 16 that are associated with clinic 254-1.

In another implementation, data aggregation module 264 may store data based on a total population of IMDs 16, i.e., data from all n of the IMDs 16 stored in datastore 204. Accordingly, data retrieval module 268 may retrieve data from datastore 204 that is representative of all of the information collected from all n of the IMDs 16. To see data relating to all n of the IMDs 16, the clinician may set a selection parameter to indicate an interest in viewing data for all n of the IMDs 16. Data retrieval module 268 may return data relating to all n of the IMDs in response to a request generated by clinician device 250 based on the selection parameter. For example, the clinician may set selection parameters to indicate an interest in viewing data related to all shocked episodes for all n of the IMDs 16 in datastore 204. Clinician device 250 may send a request to data retrieval module 268 in response to the selection. In response to the request by clinician device 250, data retrieval module 268 may retrieve data related to all shocked episodes associated with all n of the IMDs 16, such as a total number of shocked episodes and whether the shocked episodes resulted from VT/VF, SVT, noise, oversensing, or undersensing. Data retrieval module 268 may then return the requested numbers to clinician device 250 in response to the request. Clinician device 250 may then display data related to all shocked episodes associated with all n of the IMDs 16 to the clinician on a dashboard.

Although retrieving data from datastore 204 based on selection of a clinic or based on selection of all of the IMDs 16 has been described, the clinician may retrieve data relating to any subset of IMDs 16. For example, the clinician may set a selection parameter so that data retrieval module 268 retrieves data regarding any single IMD 16 of all of the IMDs 16. The clinician may also set a selection parameter that retrieves data by geographic area, such as by state, or by nation (e.g., The United States), for example. In other examples, the clinician may set selection parameters that retrieve data based on demographics (e.g., age/sex of patient 14), a length of time for which the IMD 16 has been implanted, device model, lead model, type of IMD (e.g., single/dual chamber), type of programming of the IMD 16, indications, etc. Other information that may be retrieved from datastore 204 may include atrial fibrillation burden, an average or peak ventricular rate during atrial fibrillation, a percent of right ventricular pacing, a fluid index, a rehospitalization rate of the patient, or additional information retrieved from electronic medical records.

Data aggregation module 264 may also store, and clinician devices 250 may retrieve, any type of data received from the IMDs 16. For example, data relating to a number of antitachycardia pacing (ATP) events may be stored and retrieved. Additionally, data aggregation module 264 may store, and clinician devices 250 may retrieve, marker channel data, parametric data, or other sensed physiological parameters of patient 14, such as intracardiac or intravascular pressure, activity, posture, respiration, or thoracic impedance.

FIG. 10 illustrates request and receipt of information at a single clinic (e.g., clinic 254-1) using clinician device 250-1. Clinician device 250-1 includes a user interface 280-1. User interface 280-1 may include a mouse, keyboard, and display, for example. User interface 280-1 may also include other types of interfaces, for example, a touchscreen interface. The clinician may enter selection parameters into user interface 280-1. Clinician device 250 may then send a request for information to data retrieval module 268 based on the selection parameters. Data retrieval module 268 may retrieve relevant data from datastore 204 in response to the request and process the data. Data retrieval module 268 may then send the processed data to clinician device 250-1 for display on user interface 280-1 as a dashboard.

FIG. 10 also includes a conceptual diagram of data arranged in datastore 204. Aggregate data 284 may include all of the data stored in datastore 204. For example, aggregate data 284 may include all of the data retrieved from all n of the IMDs 16, e.g., numbers of shocked episodes associated with the n IMDs 16, numbers of appropriate/inappropriate shocked episodes associated with all n IMDs 16, etc. Aggregate data 284 may also include all additional data retrieved from the n IMDs 16, such as marker channel data, parametric data, or other sensed physiological parameters of patient 14, such as intracardiac or intravascular pressure, activity, posture, respiration, or thoracic impedance.

Data stored in datastore 204 may be visualized as groups of data that are specific to each of the clinics 254. Data that is specific to a clinic 254 may include data received from IMDs 16 that are associated with clinic 254. Data that is specific to each of the clinics is illustrated as clinic specific data 288-1, 288-2, . . . , and 288-n (collectively "clinic specific data 288"). Clinic specific data 288 is illustrated as included in aggregate data 284 since clinic specific data 288 may be a subset of aggregate data 284. Clinic specific data 288-1 may represent data within the aggregate data 284 that is specific to the clinic 254-1. For example, clinic specific data 288-1 may include data from IMDs 16 associated with clinic 254-1, for example, IMDs 16 that were implanted by clinic 254-1 or receive follow-up with clinic 254-1.

Clinician device 250-1, which is associated with clinic 254-1, may send requests to data retrieval module 268 to retrieve both aggregate data 284 and clinic specific data 288-1. Data retrieval module 268 may retrieve both aggregate data 284 and clinic specific data 288-1 in response to a request from clinician device 250-1. Data retrieval module 268 may process the data retrieved from datastore 204 according to the request. For example, if the request indicates a total number of shocked episodes associated with all of the IMDs 16, data retrieval module 268 may add the total number of shocked episodes from all of the IMDs 16 in the aggregate data 284, then send the number to clinician device 250-1. As a further example, if the request indicates a total number of inappropriate shocked episodes associated with clinic 254-1, data retrieval module 268 may determine the total number of inappropriate shocked episodes that are associated with the clinic 254-1 from clinic specific data 288-1.

A selection parameter entered by the clinician, and accordingly, a request from clinician device 250-1 to remote device 200, may include a request to compare data from clinic 254-1 with data from all other clinics 254-2 to 254-n. For example, a request may indicate a desire of the clinician to compare a percentage of inappropriate shocked episodes from clinic 254-1 with a percentage of inappropriate shocked episodes from all other clinics 254-2 to 254-n. In this scenario, data retrieval module 268 may retrieve the data used for the calculations requested by the clinician. For example, data retrieval module 268 may retrieve a number of total shocked episodes and a number of inappropriate shocked episodes associated with clinic 254-1 from clinic specific data 288-1. Data retrieval module 268 may then sum a number of shocked episodes associated with each of the clinics 254-2 to 254-n and sum a number of inappropriate shocked episodes associated with clinics 254-2 to 254-n. Data retrieval module 268 may then process the data, for example, determine a percentage of inappropriate shocked episodes associated with clinic 254-1 and the other clinics 254-2 to 254-n. For example, data retrieval module 268 may determine the percentage of inappropriate shocked episodes associated with clinic 254-1 by dividing the number of inappropriate shocked episodes associated with clinic 254-1 by a total number of shocked episodes associated with clinic 254-1. Data retrieval module 268 may then determine the percentage of inappropriate shocked episodes associated with clinics 254-2 to 254-n by dividing the sum of the number of inappropriate shocked episodes associated with clinics 254-2 to 254-n by the sum of shocked episodes associated with the clinics 254-2 to 254-n. Data retrieval module 268 may then send the relevant data to clinician device 250-1. Clinician device 250-1 may then present the percentages on a dashboard on a display of user interface 280-1 for clinician review.

Although data retrieval module 268 processes data retrieved from datastore 204, e.g., determines a number, sum, and percentage of shocked episodes, this functionality could also be performed by clinician device 250. In other words, data retrieval module 268 and/or clinician device 250 may process data retrieved from datastore 204. In an implementation where processing occurs at data retrieval module 268, data retrieval module 268 may process data used in a dashboard in response to a request, then send the processed data to clinician device 250 for presentation as a dashboard. For example, data retrieval module 268 may include a web server that sends data to clinician device 250 for presentation to clinician as a webpage. In other words, a clinician may generate a dashboard in a web browser on clinician device 250 (e.g., a client) by entering selection parameters in the web browser. Data retrieval module 268 (e.g., a web server) may then serve information to clinician device 250 for display on the web browser as a dashboard.

Example dashboards are shown in FIGS. 11-14. Example dashboard 300 shown in FIG. 11 displays data in columns labeled "Clinician" and "National." The "Clinician" column may illustrate data that is specific to the clinician, or clinic, that requested data for the dashboard. The "National" column may illustrate data that has been retrieved from all of the IMDs 16 in datastore 204 (e.g., in The United States).

The row labeled "Device" may indicate a type of device for which data has been requested by the clinician. Entrust™, Concerto™, Virtuoso™, Consulta™, and Maximo™II are defibrillator devices developed by Medtronic, Inc., of Minneapolis, Minn. The row labeled "Episodes in the year" may indicate a year selected by the clinician for which to view data. The row labeled "Chamber" that includes DR, CRTD may indicate that the device type selected by the clinician includes devices that are dual chamber cardiac resynchronization therapy devices and defibrillators.

The row labeled "patients with ICDs" may indicate a number of patients associated with the clinician and a number of national patients. In other words, the clinician may be associated with 100 patients that have IMD data stored in datastore 204 and there may be data stored for 25,000 IMDs in datastore 204. The column labeled "Average Follow-up Months" may indicate an average implant time for the patients.

The row(s) labeled "# of VT/VF episodes" indicates a number of VT/VF episodes detected by IMDs 16 associated with the patients. For example, with reference to the Clinician column, the IMDs associated with Clinician delivered shocks to 120 episodes (i.e., VT/VFs as detected by IMD 16), and provided ATP therapies to 30 episodes. The "% Patients Shocked" row indicates a percentage of patients associated with the Clinician/Nation that received defibrillation shocks.

The pie charts under the "Shocked Episode Data" headings display graphically the number of appropriate/inappropriate shocked episodes. 120 shocked episodes are associated with the clinician (n=120), 60% of which were applied to VT/VF, as determined by remote device 200. In other words, 60% of the 120 shocked episodes included defibrillation shocks that were appropriately delivered. 40% of the 120 shocked episodes associated with the clinician may have been inappropriate shocked episodes, e.g., due to SVT, oversensing, or noise. Similar data is shown at the National level.

A clinician device 250 may have generated dashboard 300 based on a variety of selection parameters entered by the clinician. For example, the clinician may have indicated a desire to view data including Entrust™, Concerto™, Virtuoso™, Consulta™, and Maximo™ II devices, episodes in the year 2009, DR and CRTD devices, and a percentage of appropriate/inappropriate shocked episodes. Data retrieval module 268 may have retrieved the corresponding data from datastore 204 in response to the variety of selection parameters and clinician device 250 may have generated dashboard 300 based on the data.

Using dashboard 300, the clinician may compare their percentage of appropriate/inappropriate shocked episodes to the national data. In other words, the clinician may determine where they stand as compared to others in the nation regarding the percentage of appropriate/inappropriate shocked episodes. The dashboard 300 illustrates that clinician has a larger percentage of appropriate shocked episodes (i.e., a smaller percentage of inappropriate shocked episodes) and accordingly is performing better than the national level since a smaller percentage of inappropriate shocked episodes is desirable.

Figure 12:
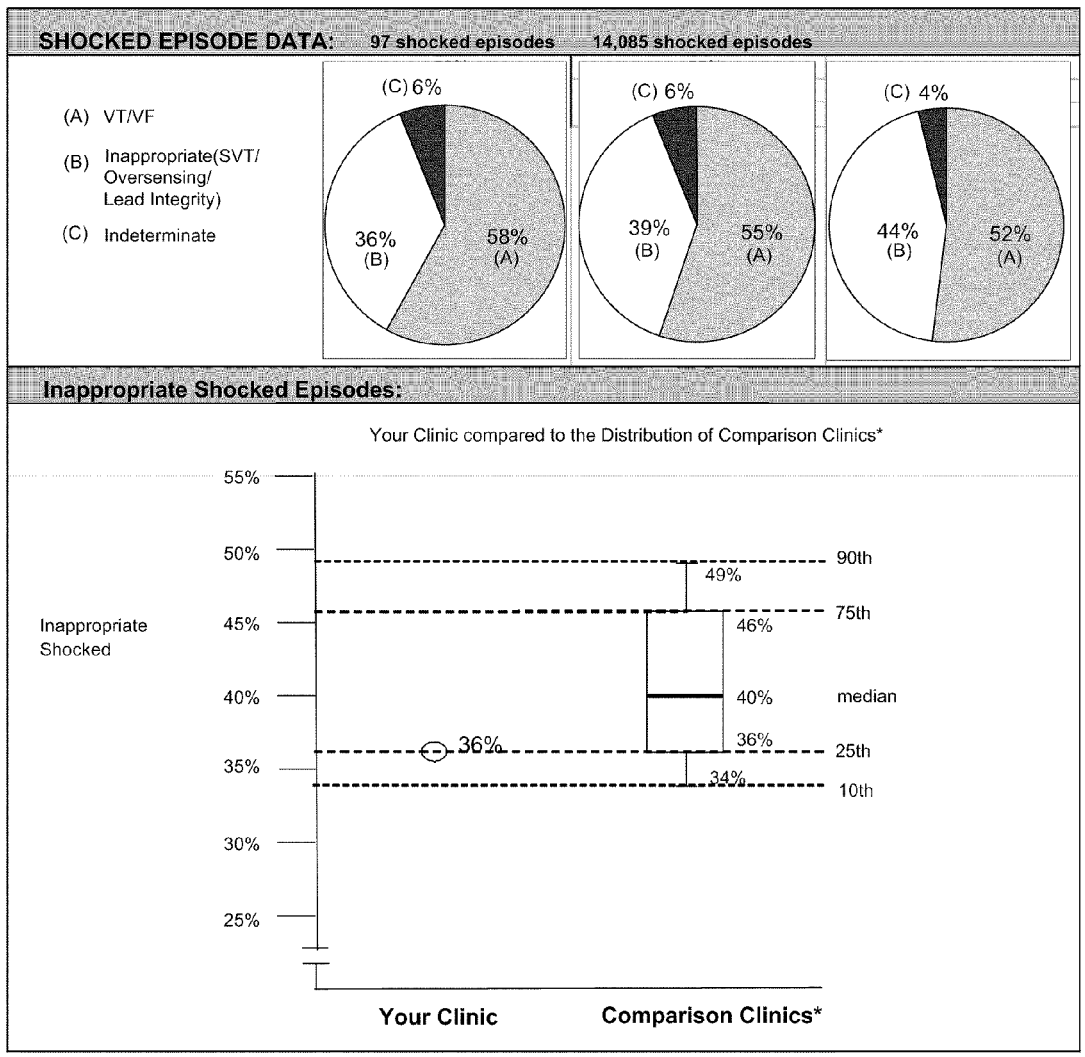
FIG. 12 illustrates another example representation of data collected by the remote device of FIG. 8.

FIG. 12 illustrates another example dashboard titled "ICD Therapy Performance Dashboard." Dashboard 302 includes three columns of data. The column labeled "Clinician" illustrates IMD data associated with the clinician/clinic that requested the data. The column labeled "Comparison Clinics" illustrates data from 59 (n=59) selected clinics. For example, the comparison clinics may be clinics that include a minimum number of patients having IMDs 16. Specifically, data for "Comparison Clinics" illustrated in dashboard 302 were selected from clinics having greater than or equal to 40 patients that have received defibrillation shocks, as noted in the footnotes of dashboard 302.

Accordingly, the clinician may enter a selection parameter that indicates a desire to view only IMD data associated with clinics having a minimum number of patients that have received defibrillation shocks. The selection parameter requesting only clinics having a minimum number of patients that received shocks may serve a variety of practical considerations. For example, data from clinics having a threshold number of patients that received defibrillation shocks may reduce noise in calculations. In other words, a larger sample of patients may cause the IMD data to be more accurate since outlier IMD data may be suppressed by the larger sample. Another source of error in measurement that the threshold may serve to overcome is error or uncertainty arising from episode classification module 260. For example, episode classification module 260 may err when classifying inappropriate/appropriate shocked episodes, i.e., classify an inappropriate shocked episode as appropriate, or visa-versa due to a mischaracterization. Observing data over a larger sample of patients (e.g., greater than 40) may reduce the impact of errors made by episode classification module 260 during classification.

Each of the columns includes data regarding a total number of patients associated with the respective columns, an average follow-up time, and a percentage of patients having tachycardia episodes that were terminated using ATP. The "SHOCKED EPISODE DATA" illustrates that the "Clinician" column includes data for 97 shocked episodes, 58% of which were appropriate shocked episodes, 36% of which were inappropriate shocked episodes, and 6% of which were indeterminate due to the uncertainty arising during analysis by episode classification module 260. "Clinician" outperformed the "Comparison Clinics" in that the percentage of appropriate shocked episodes associated with "Clinician" was greater than the "Comparison Clinics."

The "Inappropriate Shocked Episodes:" box at the bottom of dashboard 302 includes a graphical representation of the data using a box and whisker plot of inappropriate shocked episodes. The percentage of inappropriate shocked episodes for "Clinician" is illustrated at 36% on the left. The percentages of inappropriate shocked episodes for "Comparison Clinics" is illustrated as a box and whisker plot on the right. As can be seen in dashboard 302, "Clinician" performs in the top quartile relative to the "Comparison Clinics."

Figure 13:
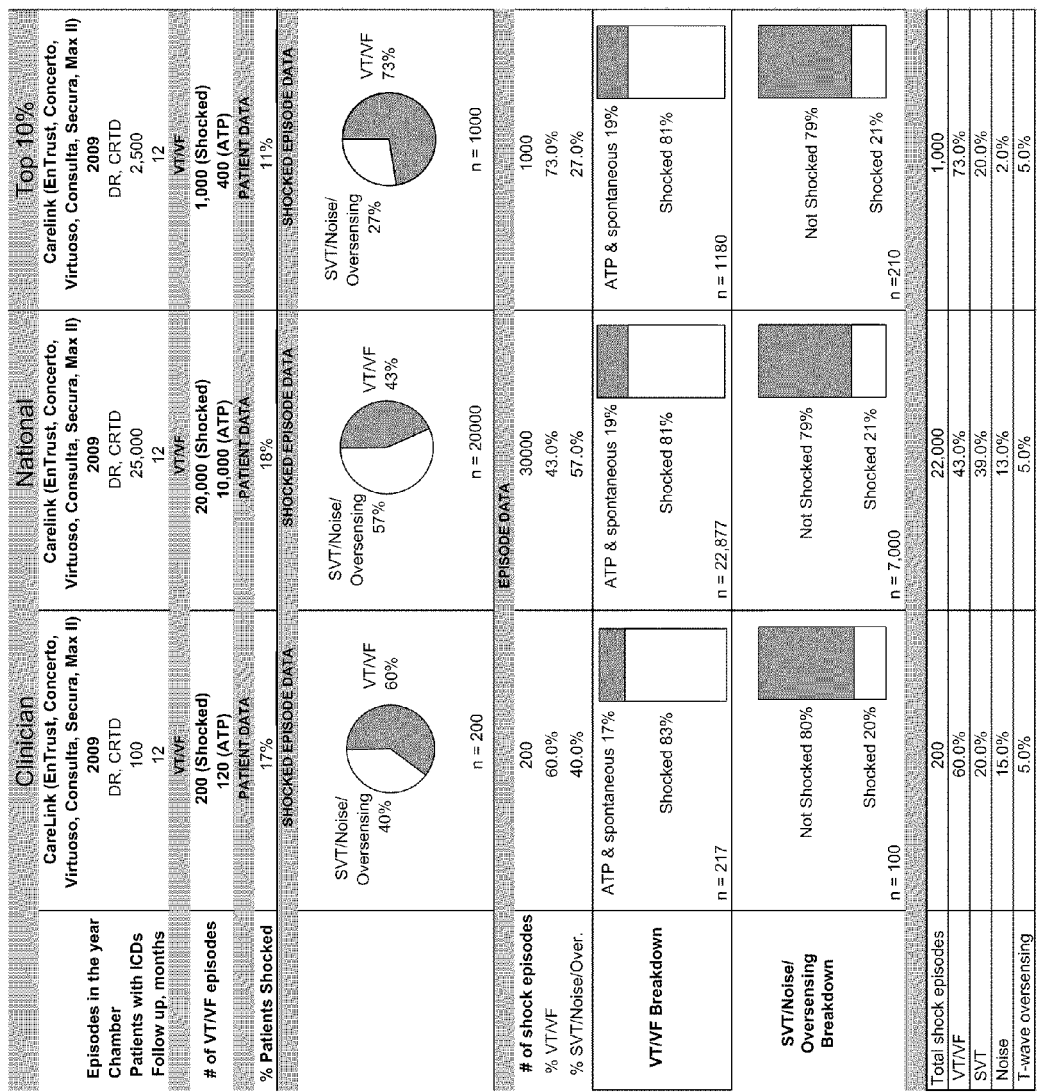
FIG. 13 illustrates another example representation of data collected by the remote device of FIG. 8.

FIG. 13 illustrates another example dashboard 304. Dashboard 304 includes 3 columns of data. The column labeled "Clinician" illustrates IMD data associated with the clinician/clinic that requested the data. The column labeled "National" may illustrate data that has been retrieved from all of the IMDs 16 in datastore 204 (e.g., in The United States). The column labeled "Top 10%" illustrates data from a top 10% of clinics in terms of the smallest percentage of inappropriate shocked episodes. In other examples, the top 10% of clinics may be selected based on the greatest percentage of appropriate shocked episodes or the lowest number of shocked episodes per patient. IMD data represented by the top 10% may be subject to other selection parameters, for example, a minimum patient per clinic parameter that selects only clinics having a minimum number of patients (e.g., 40) so that noise is reduced in calculations.

To generate the example dashboard 304, the clinician may enter a selection parameter that indicates their desire to view a top percentage (e.g., 10%) of clinics based on percentages of appropriately/inappropriately shocked episodes. Using dashboard 304, generated based on the selection parameter, the clinician may compare their percentage of appropriate/inappropriate shocked episodes to the top 10% of clinics. In other words, the clinician may determine where they stand as compared to the top clinics regarding the percentage of appropriate/inappropriate shocked episodes. The dashboard 304 illustrates that clinician has a smaller percentage of appropriately shocked episodes (i.e., a larger percentage of inappropriately shocked episodes) and accordingly may be underperforming relative to the top 10% of clinics.

Dashboard 304 also includes additional information in the rows labeled "VT/VF breakdown" and "SVT/Noise/Oversensing Breakdown." The bar graphs illustrate the breakdowns for "ATP & spontaneously" terminated VT/VF episodes, along with VT/VF episodes that were terminated using a defibrillation shock. Below the breakdowns, a table lists additional data, such as the total number of shocked episodes, percentage of shocked episodes that were VT/VF, percentage of episodes that were SVT, percentage of episodes due to noise, and percentage of episodes due to oversensing.

Figure 14:
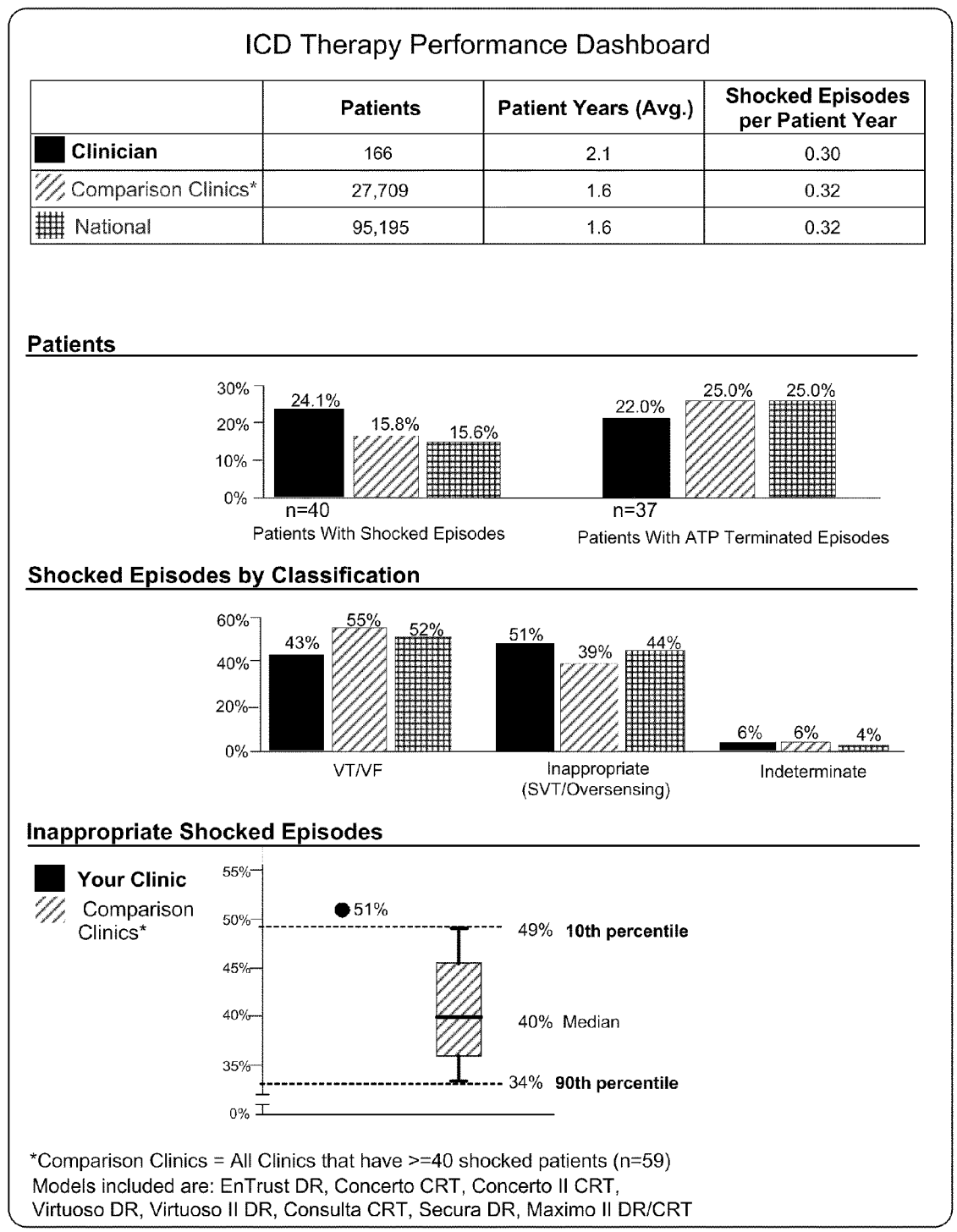
FIG. 14 illustrates another example representation of data collected by the remote device of FIG. 8.

FIG. 14 illustrates another example dashboard 305. Dashboard 305 is similar to dashboard 302 of FIG. 12. Dashboard 305 may be generated based on entry of similar selection parameters as described above with respect to FIGS. 11-13.

The top section of dashboard 305 includes three rows of data. The row labeled "Clinician" illustrates IMD data associated with the clinician/clinic that requested the data. The row labeled "Comparison Clinics" illustrates data from 59 (n=59) selected clinics. For example, the comparison clinics may be clinics that include a minimum number of patients having IMDs 16. Specifically, data for "Comparison Clinics" illustrated in dashboard 305 were selected from clinics having greater than or equal to 40 patients that have received defibrillation shocks, as noted in the footnotes of dashboard 305.

The "Patient Years (Avg.)" column illustrates an average time from date of IMD implant for the patients. The "Shocked Episodes per Patient Year" column illustrates a total number of shocked episodes divided by the total days for which patients have been followed (e.g., a sum for all devices), converted into years. For example, multiplying the number of patients by the "patient years (Avg.)" by the total number of shocked episodes per patient year will yield the total number of shocked episodes for a category. In one example, a total number of shocked episodes for "clinician" may be equal to 104 (i.e., 166×2.1×0.3).

The "Patients" section illustrates percentages of patients with shocked episodes for each of the categories. For example, 40 patients of "Clinician" had shocked episodes, therefore, 24.1% (i.e., 40/166) of patients associated with "Clinician" had shocked episodes. Similar data is illustrated for patients with ATP terminated episodes.

The "Shocked Episodes by Classification" section illustrates percentage breakdowns of classifications for each of the categories (e.g., Clinician, Comparison Clinics, National) of shocked episodes. For example, with respect to the "Clinician", 43% of shocked episodes were appropriately delivered, 51% of shocked episodes were inappropriately delivered, and 6% of shocked episodes were classified as indeterminate due to the uncertainty arising during analysis by episode classification module 260. "Clinician" did not outperform the "Comparison Clinics" in that the percentage of appropriate/inappropriate shocked episodes associated with "Clinician" was less/greater than the "Comparison Clinics."

The "Inappropriate Shocked Episodes" section at the bottom of dashboard 305 includes a graphical representation of the data using a box and whisker plot of inappropriate shocked episodes. The percentage of inappropriate shocked episodes for "Clinician" is illustrated as 51% (the solid dot). The percentages of inappropriate shocked episodes for "Comparison Clinics" are illustrated as a box and whisker plot. As can be seen in dashboard 305, "Clinician" performs at less than the $10^{th}$ percentile relative to the "Comparison Clinics."

In some examples, shocked episode data, as illustrated in FIGS. 11-14, may be skewed if certain patients experience a relatively greater number of shocked episodes relative to other patients included in the shocked episode data. For example, if shocked episode data represents a clinic including 5 patients and one of the patients experiences a significant number of shocked episodes, then shocked episode data representing that clinic may be skewed by the patient that experienced the significant number of shocks.

FIGS. 15A-B illustrate how a patient that experiences a significant number of shocked episodes may skew the shocked episode data reported in the dashboard. The tables shown in FIGS. 15A-B show example data that may have been requested and received by a clinician device 250. Specifically, the data shown in FIGS. 15A-B illustrate numbers of appropriate, inappropriate, and indeterminate shocked episodes for patients A-E of a single clinic. The clinician device that requested the data shown in FIGS. 15A-B may have also determined the percentages, total episode numbers, and corresponding normalized data shown in FIGS. 15A-B.

FIG. 15A illustrates a scenario where none of the patients experienced a significantly greater number of shocked episodes, and therefore, the data is not substantially skewed. FIG. 15B illustrates a contrasting scenario where one patient experienced a significantly greater number of shocked episodes relative to other patients in the group and therefore the shocked episode data reported in the dashboard may be skewed.

Referring now to FIG. 15A, a table shows data for five example patients A-E of a clinic. The columns of the chart list the number of appropriate shocked episodes, inappropriate shocked episodes, and indeterminate shocked episodes, as determined by episode classification module 260. A total of 10 episodes are associated with the clinic. The row labeled "Total" illustrates a sum of each of the columns. The row labeled "Percent" shows the percentage makeup of each of the categories within the clinic. A clinician device 250 may determine the "Percent" row by dividing the total of each column (e.g., 6, 3, 1) by the total number of episodes (i.e., 10) associated with the clinic. The table of FIG. 15A includes patients having a relatively similar number of shocked episodes. As such, none of the patients A-E substantially skew the shocked episode data that may be reported in the dashboard.

In contrast to FIG. 15A, the data included in FIG. 15B illustrates a scenario where shocked episodes associated with patient E may skew shocked episode data associated with the clinic (e.g., all of patients A-D). For example, patient E in FIG. 15B experienced 10 appropriate shocked episodes, which is 10 times greater than any of the other patients A-D.

Accordingly, as compared to FIG. 15A patient E experienced a substantially greater number of appropriate shocked episodes relative to patients A-D, and therefore data associated with patient E may be viewed as skewing the shocked episode data as reported in a dashboard.

A clinician device 250 may process the shocked episode data to reduce a skewing effect caused by patients having a disproportionate number of shocked episodes. For example, a clinician device 250 may normalize the data illustrated in FIG. 15B in order to prevent the skewing of data that may be caused by patient E. According to an example normalization operation, clinician device 250 may normalize each of the rows of data for patients A-E. For example, clinician device 250 may sum the total number of shocks in each row, then divide each of the columns in that row by the sum. According to the data in FIG. 15B, patient A experienced 1 shocked episode, the shocked episode being an appropriate shocked episode. Accordingly, normalized data for patient A includes a "1" in the appropriate shocked episode column in the table on the right. According to the data in FIG. 15B, patient C experienced 3 shocked episodes, 1 of each category. Accordingly, normalized data for patient C includes a "⅓" in each column in the table on the right, in other words, each column is associated with ⅓ of the total shocked episodes experienced by patient C. According to the data in FIG. 15B, patient E experienced 10 shocked episodes, all shocked episodes being appropriate shocked episodes. Accordingly, normalized data for patient E includes a "1" in the appropriate shocked episode column in the table on the right, i.e., 10 appropriate shocked episodes out of 10 total episodes. Clinician device 250 may determine the percentage breakdown of each of the categories (i.e., appropriate, inappropriate, indeterminate) by dividing each of the totals for each category by the sum of all of the totals (i.e., 5). As can be seen in the table on the right in FIG. 15B, the normalization operation resulted in percentages that are not as skewed towards data associated with the patient having a disproportionate number of shocked episodes. In other words, the percentages in the table on the right of FIG. 15B are more similar to the table of FIG. 15A, which is not skewed, than the percentages in the table on the left of FIG. 15B.

In other implementations, clinician device 250 may compensate for data that skews overall results using other techniques. For example, clinician device 250 may exclude, from calculations, any patient data that indicates a relatively greater number of shocked episodes. According to this example, clinician device 250 may exclude data for patients having more than a threshold number of shocked episodes.

Figure 16:
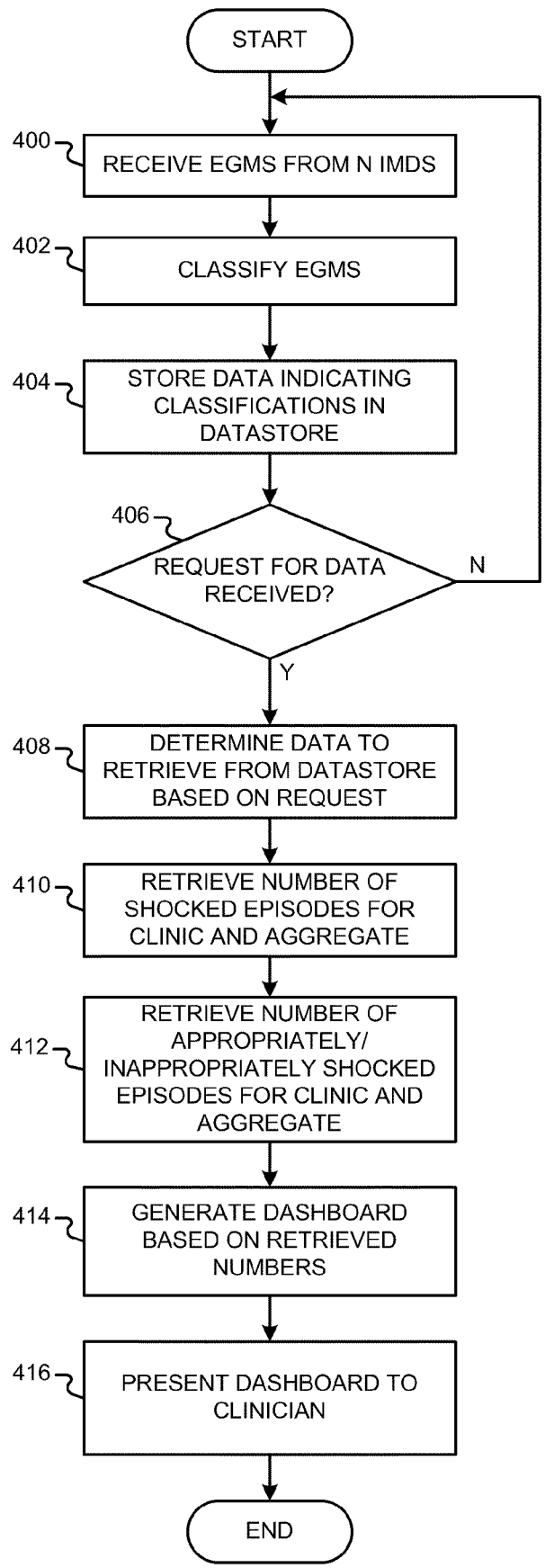
FIG. 16 illustrates an example method for generating a dashboard according to the present disclosure.

Referring now to FIG. 16, a method for generating a dashboard is shown. Remote device 200 receives EGMs and other data, e.g., associated with episodes, from n IMDs 16 via a network (400). Episode classification module 260 classifies each of the episodes including defibrillation shocks (i.e., classifies each of the shocked episodes) (402). For example, episode classification module 260 may classify the episodes as one of VT, VF, SVT, and oversensing. Data aggregation module 264 stores data indicating the classifications in datastore 204 (404). Data retrieval module 268 determines whether a request for data has been received from a clinician device 250 (406). For example, the request may have been generated by a clinician using clinician device 250. If data retrieval module 268 determines that a request for data has not been received, the method continues at (400).

If data retrieval module 268 determines that a request has been received, data retrieval module 268 determines which data to retrieve from datastore 204 based on the request (408). For example, the data request may indicate a desire by the clinician to view data regarding a percentage of appropriate/inappropriate shocked episodes associated with their clinic relative to national data. Data retrieval module 268 retrieves a number of shocked episodes associated with clinician's clinic and a number of shocked episodes associated with aggregate data 284 (410). Data retrieval module 268 retrieves data relating to a number of appropriate/inappropriate shocked episodes associated with clinician's clinic and with aggregate data 284 (412). A dashboard is then generated based on the retrieved numbers (414). Clinician device 250 then presents the dashboard to a clinician (416).

Although the disclosure is described with respect to an implantable cardiac device, the techniques described may be applicable to other implantable devices, such as devices that provide spinal cord stimulation, deep brain stimulation, pelvic floor stimulation, gastric stimulation, occipital stimulation, functional electrical stimulation, and the like. Accordingly, the techniques described herein may be applicable to non-cardiac signals received from electrodes or sensors located on or within a patient. As an example, remote device 200 may receive EEG waveforms from IMDs, and analyze the EEG waveforms to determine whether delivery or non-delivery of therapy by the IMDs based on the EEG waveforms, e.g., in response to detection of a seizure or disordered movement, was appropriate. Remote device 200 may provide information to a requesting device or user illustrating the degree of appropriate or inappropriate therapy delivery or non-delivery of such therapies by such IMDs for one or more groups of the IMDs.

Furthermore, although described with respect to an implantable medical device that delivers therapy, the techniques of the disclosure may be applicable to implantable medical devices that do not deliver therapy, such as implantable monitors. For example, the techniques of the disclosure may be applicable to insertable cardiac monitors that monitor heart rhythms and record ECGs associated with physiological events, e.g., fainting.

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components. The term "processor" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A system comprising:
   an episode classification module that:
   receives electrogram waveforms (EGMs) from N implantable medical devices (IMDs), wherein N is an integer greater than 1;
   determines whether the EGMs are associated with one or more deliveries of therapy by the N IMDs;
   analyzes at least some of the EGMs; and
   determines whether the one or more deliveries or non-deliveries of therapy by the IMDs in response to rhythms included in the EGMs were appropriate based on the analysis; and
   a data retrieval module that:
   receives a comparison request from a computing device, via a network, the comparison request indicating at least two groups of the N IMDs and a type of comparison to be made between the at least two groups; and
   provides to the computing device via the network, in response to the comparison request, data for presentation of a comparison between the at least two groups on the computing device, wherein the data indicates, for each of the groups, at least one of how many of the one or more deliveries or non-deliveries of therapy were appropriate, or how many of the one or more deliveries or non-deliveries of therapy were inappropriate.

2. The system of claim 1, wherein the EGMs include cardiac electrograms, the N IMDs include implantable cardioverter-defibrillators, and the deliveries of therapy include deliveries of at least one of defibrillation shocks or cardioversion shocks.

3. The system of claim 2, wherein the episode classification module determines whether the EGMs indicate ventricular tachyarrhythmia based on the analysis, and determines whether the one or more deliveries or non-deliveries of therapy were appropriate based on the determinations.

4. The system of claim 3, wherein the episode classification module determines whether the EGMs indicate ventricular tachycardia, ventricular fibrillation, supraventricular tachycardia, oversensing, or undersensing based on the analysis, and determines whether the one or more deliveries or non-deliveries of therapy were appropriate based on the determinations.

5. The system of claim 2, wherein the episode classification module determines whether the EGMs indicate one of atrial fibrillation, sinus tachycardia, atrial flutter, atrial tachycardia, or lead fracture noise based on the analysis, and wherein the episode classification module determines whether the one or more deliveries or non-deliveries of therapy were appropriate based on the determinations.

6. The system of claim 1, wherein the episode classification module classifies at least one of the one or more deliveries of therapy as indeterminate to indicate that the delivery may not be accurately classified by the episode classification module as appropriate or inappropriate.

7. The system of claim 1, wherein the episode classification module receives at least one of the EGMs via the network.

8. The system of claim 1, wherein the network includes the Internet.

9. The system of claim 1, wherein the episode classification module determines which of the EGMs are associated with one or more deliveries of therapy based on marker channel data from the N IMDs.

10. The system of claim 1, wherein a first group of the at least two groups is associated with a first clinic, wherein a second group of the at least two groups is associated with a plurality of patients associated with other clinics, and wherein the data retrieval module provides data for presentation of a comparison between the first group and the second group.

11. The system of claim 1, wherein the data retrieval module provides to the computing device data indicating, for each of the groups, how many of the EGMs precipitated deliveries of therapy.

12. The system of claim 1, wherein a first group of the at least two groups is associated with a particular clinic or clinician.

13. The system of claim 12, wherein a second group of the at least two groups is associated with IMDs other than those in the first group, and wherein the data retrieval module provides data for presentation of a comparison between the first group and the second group.

14. The system of claim 1, wherein the comparison request includes at least one selection parameter, and wherein one of the at least two groups is defined by the selection parameter.

15. The system of claim 14, wherein the at least one selection parameter includes at least one of a geographical area, a patient demographic, a number of patients associated with a clinic, an IMD type, an IMD model, a lead model, an amount of time implanted for the IMDs, a disease or disorder indication, an atrial fibrillation burden, an average or peak ventricular rate during atrial fibrillation, a percent of right ventricular pacing, a fluid index, or a rehospitalization rate of the patient.

16. A method comprising:
   receiving electrogram waveforms (EGMs) from N implantable medical devices (IMDs), wherein N is an integer greater than 1;
   determining whether the EGMs are associated with one or more deliveries of therapy by the N IMDs;
   analyzing at least some of the EGMs;
   determining whether the one or more deliveries or non-deliveries of therapy by the IMDs in response to rhythms included in the EGMs were appropriate based on the analysis;
   receiving a comparison request from a computing device, via a network, the comparison request indicating at least two groups of the N IMDs and a type of comparison to be made between the at least two groups; and
   providing to the computing device via the network, in response to the comparison request, data for presentation of a comparison between the at least two groups on the computing device, wherein the data indicates, for each of the groups, at least one of how many of the one or more deliveries or non-deliveries of therapy were appropriate, or how many of the one or more deliveries or non-deliveries of therapy were inappropriate.

17. The method of claim 16, wherein the EGMs include cardiac electrograms, the N IMDs include implantable cardioverter-defibrillators, and the deliveries of therapy include deliveries of at least one of defibrillation shocks or cardioversion shocks.

18. The method of claim 17, further comprising:
   determining whether the EGMs indicate ventricular tachyarrhythmia based on the analysis; and
   determining whether the one or more deliveries or non-deliveries of therapy were appropriate based on the determinations.

19. The method of claim 18, further comprising:
  determining whether the EGMs indicate ventricular tachycardia, ventricular fibrillation, supraventricular tachycardia, oversensing, or undersensing based on the analysis; and
  determining whether the one or more deliveries or non-deliveries of therapy were appropriate based on the determinations.

20. The method of claim 17, further comprising:
  determining whether the EGMs indicate one of atrial fibrillation, sinus tachycardia, atrial flutter, atrial tachycardia, or lead fracture noise based on the analysis; and
  determining whether the one or more deliveries or non-deliveries of therapy were appropriate based on the determinations.

21. The method of claim 16, further comprising classifying at least one of the one or more deliveries of therapy as indeterminate to indicate that the delivery may not be accurately classified as appropriate or inappropriate.

22. The method of claim 16, further comprising receiving at least one of the EGMs via the network.

23. The method of claim 16, further comprising determining which of the EGMs are associated with one or more deliveries of therapy based on marker channel data from the N IMDs.

24. The method of claim 16, wherein a first group of the at least two groups is associated with a first clinic, wherein a second group of the at least two groups is associated with a plurality of patients associated with other clinics, and wherein providing data for presentation further comprises providing data for presentation of a comparison between the first group and the second group.

25. A system comprising:
  means for receiving electrogram waveforms (EGMs) from N implantable medical devices (IMDs), wherein N is an integer greater than 1;
  means for determining whether the EGMs are associated with one or more deliveries of therapy by the N IMDs;
  means for analyzing at least some of the EGMs;
  means for determining whether the one or more deliveries or non-deliveries of therapy by the IMDs in response to rhythms included in the EGMs were appropriate based on the analysis;
  means for receiving a comparison request from a computing device, via a network, the comparison request indicating at least two groups of the N IMDs and a type of comparison to be made between the at least two groups; and
  means for providing to the computing device via the network, in response to the comparison request, data for presentation of a comparison between the at least two groups on the computing device, wherein the data indicates, for each of the groups, at least one of how many of the one or more deliveries or non-deliveries of therapy were appropriate, or how many of the one or more deliveries or non-deliveries of therapy were inappropriate.

26. The system of claim 25, wherein the EGMs include cardiac electrograms, the N IMDs include implantable cardioverter-defibrillators, and the deliveries of therapy include deliveries of at least one of defibrillation shocks or cardioversion shocks.

27. The system of claim 26, further comprising:
  means for determining whether the EGMs indicate ventricular tachyarrhythmia based on the analysis; and
  means for determining whether the one or more deliveries or non-deliveries of therapy were appropriate based on the determinations.

28. The system of claim 27, further comprising:
  means for determining whether the EGMs indicate ventricular tachycardia, ventricular fibrillation, supraventricular tachycardia, oversensing, or undersensing based on the analysis; and
  means for determining whether the one or more deliveries or non-deliveries of therapy were appropriate based on the determinations.

29. A computer-readable storage medium comprising instructions that cause a programmable processor to:
  receive electrogram waveforms (EGMs) from N implantable medical devices (IMDs), wherein N is an integer greater than 1;
  determine whether the EGMs are associated with one or more deliveries of therapy by the N IMDs;
  analyze at least some of the EGMs;
  determine whether the one or more deliveries or non-deliveries of therapy by the IMDs in response to rhythms included in the EGMs were appropriate based on the analysis;
  receive a comparison request from a computing device, via a network, the comparison request indicating at least two groups of the N IMDs and a type of comparison to be made between the at least two groups; and
  provide to the computing device via the network, in response to the comparison request, data for presentation of a comparison between the at least two groups on the computing device, wherein the data indicates, for each of the groups, at least one of how many of the one or more deliveries or non-deliveries of therapy were appropriate, or how many of the one or more deliveries or non-deliveries of therapy were inappropriate.

30. The computer-readable storage medium of claim 29, wherein the EGMs include cardiac electrograms, the N IMDs include implantable cardioverter-defibrillators, and the deliveries of therapy include deliveries of at least one of defibrillation shocks or cardioversion shocks.

31. The computer-readable storage medium of claim 30, further comprising instructions that cause the programmable processor to:
  determine whether the EGMs indicate ventricular tachyarrhythmia based on the analysis; and
  determine whether the one or more deliveries or non-deliveries of therapy were appropriate based on the determinations.

32. The computer-readable storage medium of claim 31, further comprising instructions that cause the programmable processor to:
  determine whether the EGMs indicate ventricular tachycardia, ventricular fibrillation, supraventricular tachycardia, oversensing, or undersensing based on the analysis; and
  determine whether the one or more deliveries or non-deliveries of therapy were appropriate based on the determinations.

* * * * *